United States Patent
Kimura

(10) Patent No.: US 9,535,147 B2
(45) Date of Patent: Jan. 3, 2017

(54) MAGNETIC RESONANCE IMAGING APPARATUS

(71) Applicant: TOSHIBA MEDICAL SYSTEMS CORPORATION, Otawara-Shi (JP)

(72) Inventor: Tokunori Kimura, Yaita (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 12 days.

(21) Appl. No.: 14/053,765

(22) Filed: Oct. 15, 2013

(65) Prior Publication Data

US 2014/0035583 A1 Feb. 6, 2014

Related U.S. Application Data

(62) Division of application No. 12/507,317, filed on Jul. 22, 2009, now Pat. No. 8,588,890.

(30) Foreign Application Priority Data

Jul. 24, 2008 (JP) .................................. 2008-190967
Apr. 10, 2009 (JP) .................................. 2009-096183
Jun. 5, 2009 (JP) .................................. 2009-136251

(51) Int. Cl.
*A61B 5/055* (2006.01)
*G01R 33/56* (2006.01)
(Continued)

(52) U.S. Cl.
CPC ............... *G01R 33/56* (2013.01); *A61B 5/055* (2013.01); *G01R 33/5615* (2013.01);
(Continued)

(58) Field of Classification Search
CPC . G01R 33/56; G01R 33/5635; G01R 33/5615; G01R 33/5607; G01R 33/56316; G01R 33/5601; G01R 33/5608; A61B 5/055
See application file for complete search history.

(56) References Cited

U.S. PATENT DOCUMENTS 4,754,223 A 6/1988 In Den Kleef et al.
5,225,779 A 7/1993 Parker et al.
(Continued)

FOREIGN PATENT DOCUMENTS

JP 4-053531 2/1992

OTHER PUBLICATIONS

Partial European search report and communication of same in EP 09009333.7 dated Mar. 2, 2010.
(Continued)

*Primary Examiner* — Jonathan Cwern
(74) *Attorney, Agent, or Firm* — Nixon & Vanderhye P.C.

(57) ABSTRACT

First and second magnetization vectors are detected for each pixel position in an imaging region including at least part of a subject, the magnetization vector being excited to have a phase difference between a flow portion and a static portion or between a normal portion and an abnormal portion. First and second pixel values at each pixel position are determined as a value proportional to an absolute value of the respectively corresponding amplitudes of the first and second magnetization vectors detected for each of the pixel positions. On the basis of a real part or phase of the magnetization vectors detected for each of the pixel positions, the determined pixel values are corrected so that the difference of pixel values corresponding to third pixel values increases between (a) the flow portion or the abnormal portion and (b) the static portion or the normal portion.

9 Claims, 18 Drawing Sheets

(51) Int. Cl.
G01R 33/561 (2006.01)
G01R 33/563 (2006.01)
(52) U.S. Cl.
CPC ...... *G01R 33/5635* (2013.01); *G01R 33/5601* (2013.01); *G01R 33/5607* (2013.01); *G01R 33/5608* (2013.01); *G01R 33/56316* (2013.01)

(56) References Cited

U.S. PATENT DOCUMENTS

| | | | |
|---|---|---|---|
| 6,501,272 | B1 | 12/2002 | Haacke et al. |
| 6,658,280 | B1 | 12/2003 | Haacke |
| 7,103,490 | B2 | 9/2006 | Deimling |
| 2003/0212322 | A1 | 11/2003 | Haacke |
| 2008/0071167 | A1 | 3/2008 | Ikedo |
| 2008/0119721 | A1 | 5/2008 | Kimura et al. |
| 2009/0076374 | A1 | 3/2009 | Kimura |

OTHER PUBLICATIONS

Suri, et al., "A Review on MR Vascular Image Processing Algorithms: Acquisition and Prefiltering: Part I," *IEEE Transactions on Information Technology in Biomedicine*, IEEE Service Center, Los Alamitos, CA, US, vol. 6, No. 4, Dec. 1, 2002, XP 011074850, ISSN: 1089-7771.

Crowe, et al., "Elimination of residual blood flow-related signal in 3D volume-selective TSE arterial wall imaging using velocity-sensitive phase reconstruction," *Journal of Magnetic Resonance Imaging*, Society for Magnetic Resonance Imaging, Oak Brook, IL, US, vol. 23, No. 3, pp. 416-421, Mar. 1, 2006, XP007910377, ISSN: 1053-1807.

Pelc, et al.: "Encoding Strategies for Three-Direction Phase-Contrast MR Imaging of Flow," *Journal of Magnetic Resonance Imaging*, Society for Magnetic Resonance Imaging, Oak Brook, IL, US, vol. 1, No. 4, pp. 405-413, Jul. 1, 1991, XP009060150, ISSN: 1053-1807.

Communication of Extended European Search Report in EP 09 00 9333.7 dated Jun. 22, 2010.

Extended European Search Report in EP 09009333 dated Jun. 15, 2010.

Office Action in EP 11 151 529.2-2209 dated Dec. 28, 2011.

Reichenbach, et al., "High-resolution venography of the brain using magnetic resonance imaging," *Magnetic Resonance Materials in Physics, Biology and Medicine*, vol. 6, pp. 62-69, Jun. 1, 1998, XP002971990.

Reichenbach, et al., "High-resolution BOLD venographic imaging: a window into brain function," *NMR in Biomedicine*, vol. 14, pp. 453-467; Jan. 1, 2001, XP002474050.

Koopmans, Peter J., et al., "MR venography of the human brain using susceptibility weighted imaging at very high field strength," *Magnetic Resonance Materials in Physics, Biology and Medicine*, vol. 21, No. 1-2, pp. 149-158, Jan. 11, 2008, XP019596821.

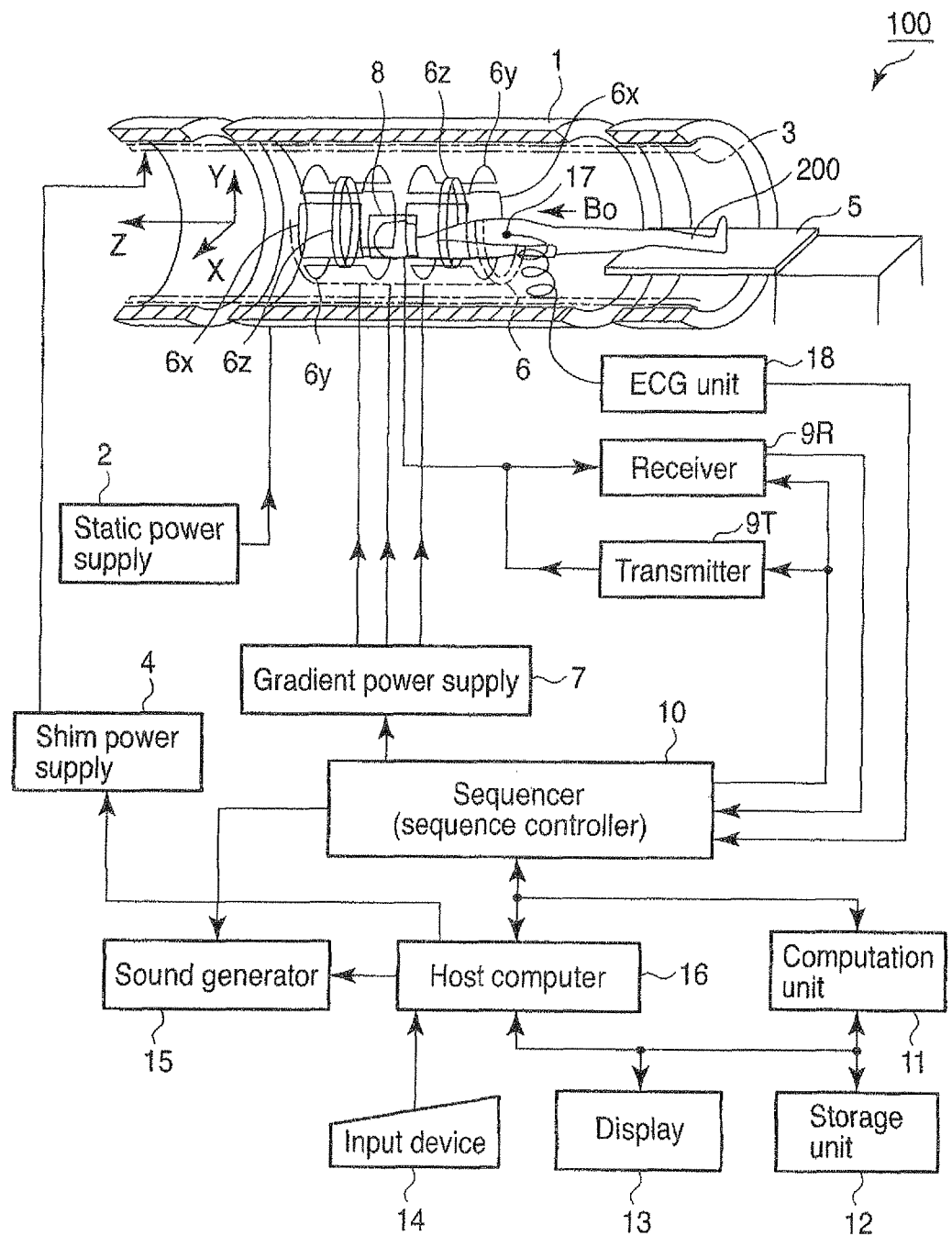
F I G. 1

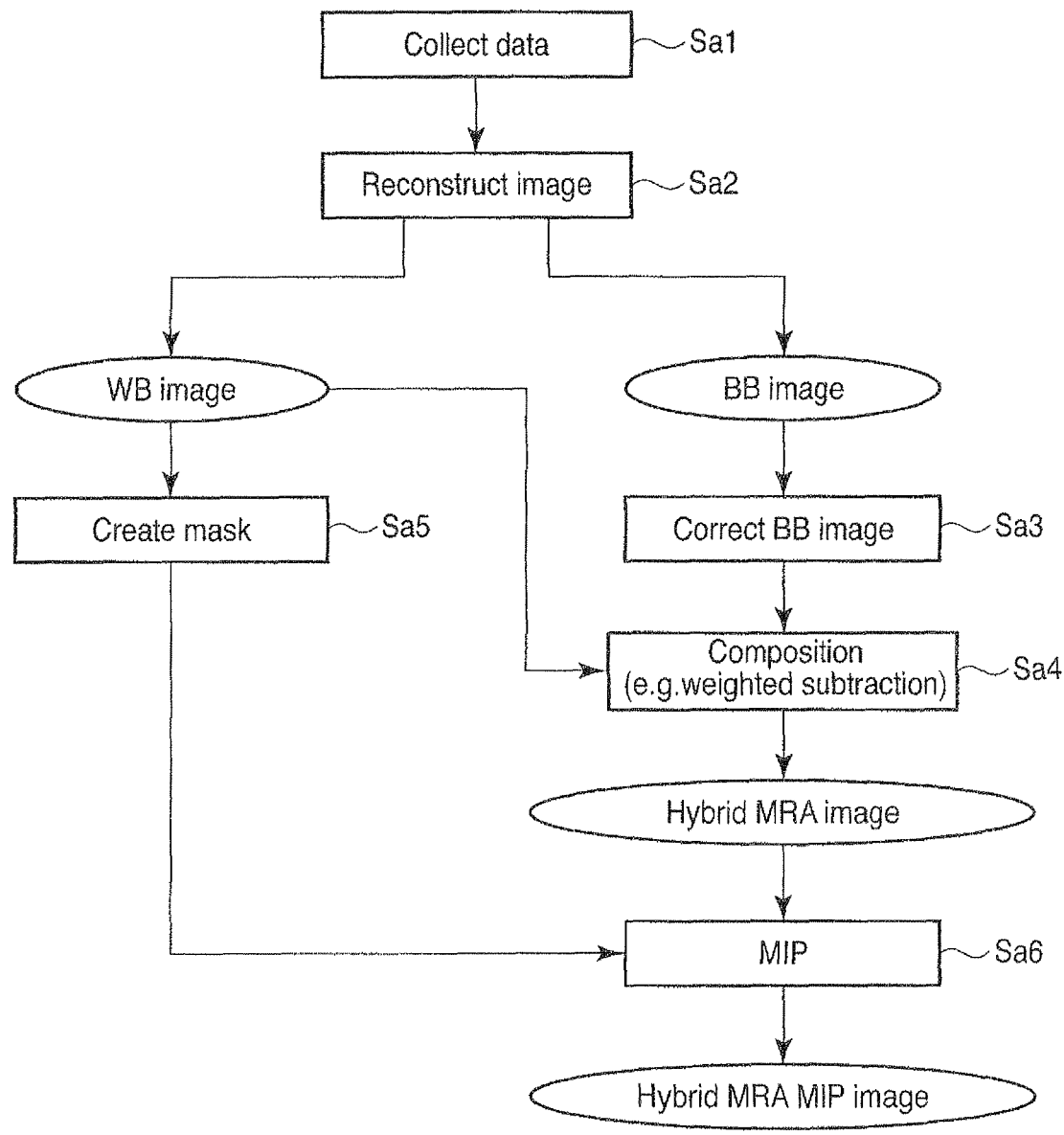
F I G. 2

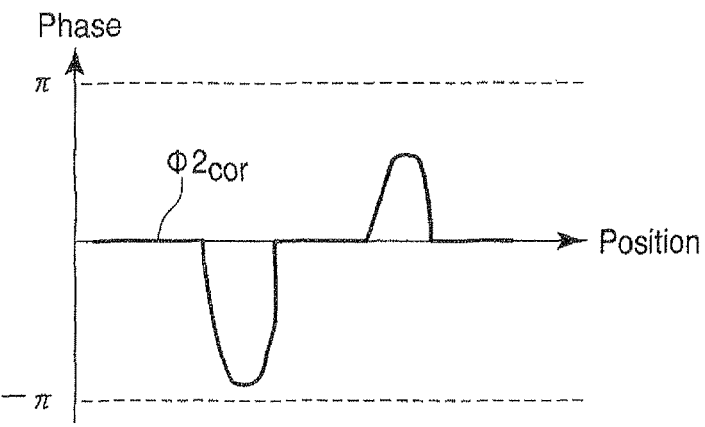
F I G. 18
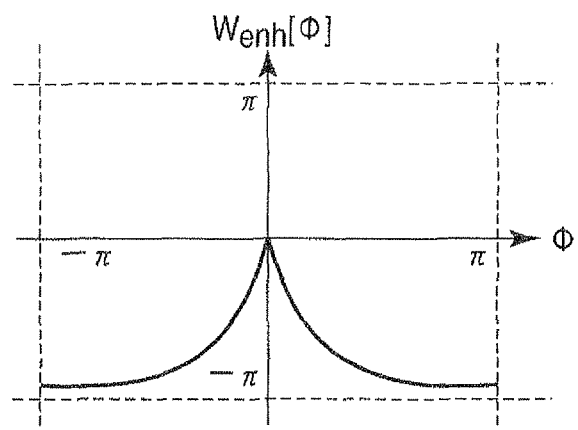
F I G. 19
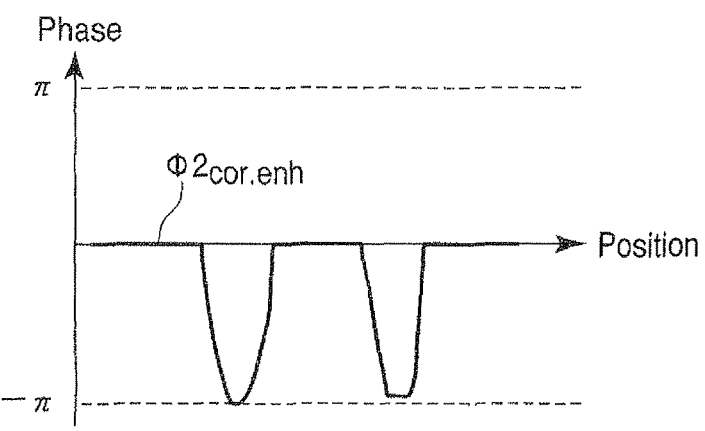
F I G. 20

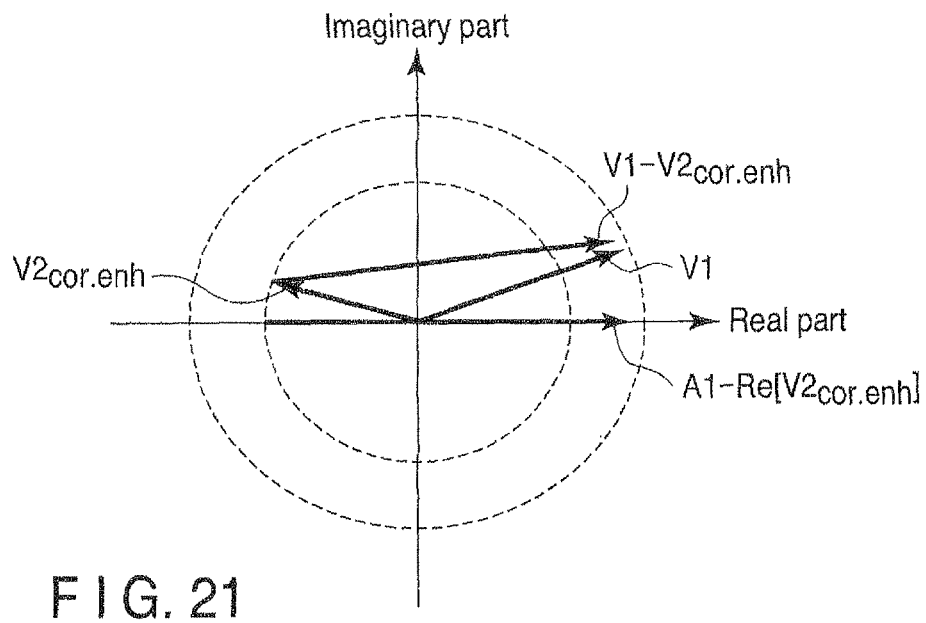
F I G. 21
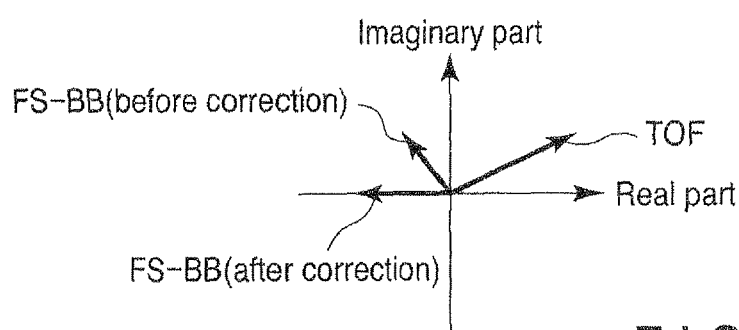
F I G. 22
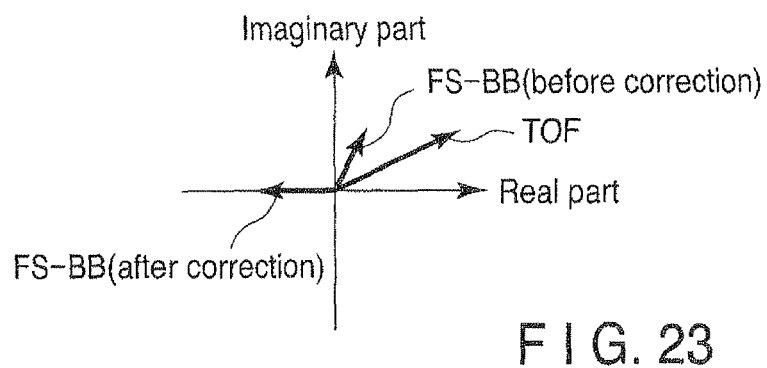
F I G. 23

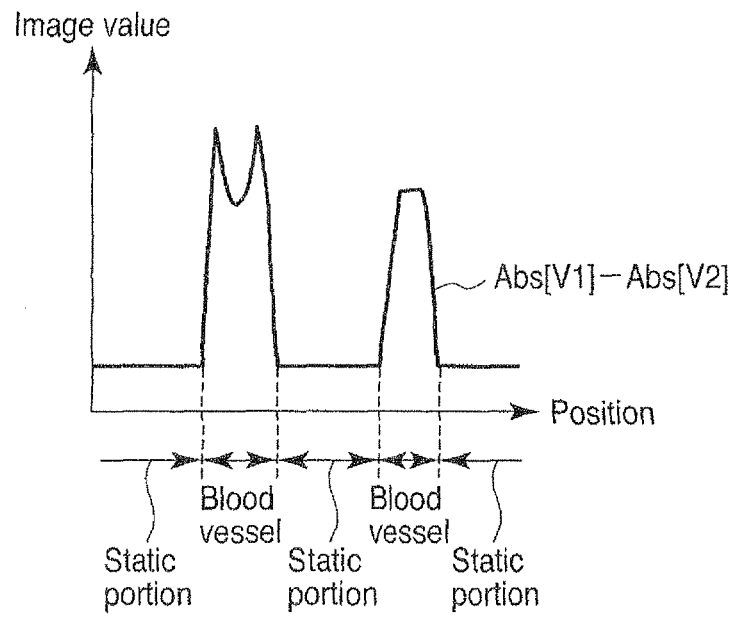
F I G. 26
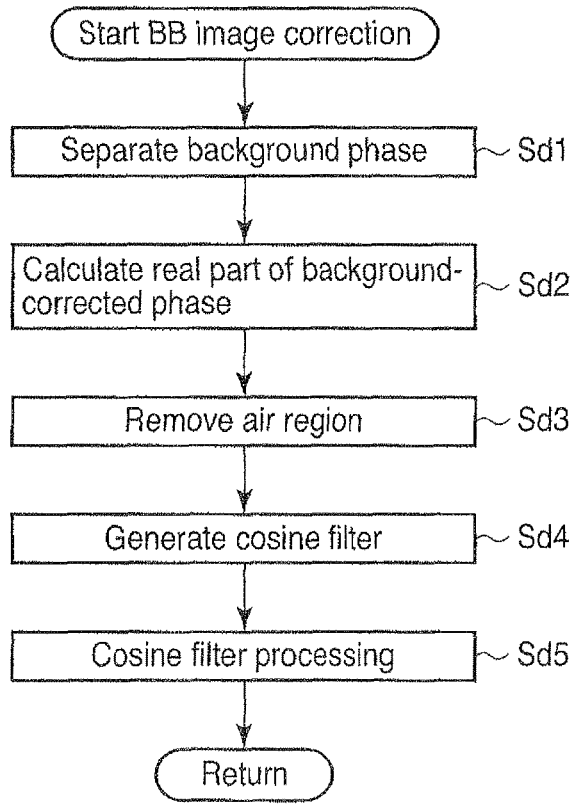
F I G. 27

F I G. 29

MAGNETIC RESONANCE IMAGING APPARATUS

CROSS-REFERENCE TO RELATED APPLICATIONS

This is a division of application Ser. No. 12/507,317 filed Jul. 22, 2009 (now U.S. Pat. No. 8,588,890), which is based upon and claims the benefit of priority under 35 U.S.C. §119 from prior Japanese Patent Applications No. 2008-190967 filed Jul. 24, 2008; No. 2009-096183 filed Apr. 10, 2009; and No. 2009-136251 filed Jun. 5, 2009, the entire contents of all of which are incorporated herein by reference.

CROSS-REFERENCE TO RELATED APPLICATIONS

BACKGROUND

1. Technical Field

The present exemplary embodiments relate to a magnetic resonance imaging (MRI) apparatus that generates an image by showing a flow portion such as a blood vessel in which a fluid flows clearer than a static portion or by showing a tissue different in susceptibility from a normal tissue clearer than a normal tissue.

2. Related Art

A magnetic resonance imaging method for arteries and veins, that is, MR angiography (MRA) includes a time of flight (TOF) method using a gradient echo (GRE) method, and a black-blood (BB) method using a fast spin echo (FSE) method for imaging a blood vessel at low signal intensity. Recently, a susceptibility-weighted imaging (SWI) method that applies the susceptibility effect of veins has become available.

A non-contrast TOF method is a typical example of a white-blood (WB) method. The non-contrast TOF method utilizes an in-flow effect, so that an artery with a high flow velocity close to an inflow part of a slab has high signal intensity. In this non-contrast TOF method, it is difficult to visualize turbulent parts, and peripheral blood vessels such as perforating branches are not easily visualized, thus arteries are principally visualized. When an image is taken with a T1-weighted (T1W) sequence using a paramagnetic contrast agent, blood vessels are visualized at high signal intensity, which means a WB method. In addition, an MRA method in which blood vessels show higher signal intensity than background tissues is generally referred to as the WB method here.

In the BB method, blood vessels show lower signal intensity than peripheral tissues, slow blood flows are also visualized, and blood vessel walls are correctly visualized. It is also possible in the BB method to visualize the turbulent parts that are difficult to visualize in the TOF method. The sequence of the BB method was initially developed by using the FSE method, but is not used very widely due to the problem of image processing or other. In the BB method, while both arterial blood and venous blood show low signal intensity, arteries can be emphasized by setting a slightly shorter echo time (TE). In addition, when an image is taken with a T2*-weighted (T2*W) based sequence using the paramagnetic contrast agent, blood vessels are visualized at low signal intensity, which means the BB method.

In the BB method, peripheral tissues show low signal intensity and it is, therefore, difficult to separately extract the blood vessels alone. For example, it is difficult to exclude air by minimum intensity projection (minIP) in the BB method. The blood vessels can be relatively easily extracted in the WB method by, for example, maximum intensity projection (MIP).

Another known MRA method is a phase contrast method. The phase contrast method achieves imaging by using the amplitudes and phases of two sets of signals that have been collected after a gradient magnetic field is used as a bipolar gradient so that the polarities of these signals are the reverse of each other.

While MRA is an imaging method for obtaining an image in which a flow portion and a static portion are shown with a contrast therebetween, there is also known an imaging method different from the MRA that obtains an image that shows the difference of susceptibility as a contrast. For example, an imaging method is known that obtains an image that shows an abnormal tissue such as a bleeding tissue and normal tissues around the abnormal tissue with a contrast therebetween.

Various methods as described above have heretofore been known to show the flow portion and the static portion or the abnormal tissue and the normal tissue with a contrast therebetween. However, for accurate or efficient medical diagnoses, there has been a demand for an image that provides a greater contrast to show the flow portion or the abnormal tissue more clearly.

Moreover, a technique described in the specification of U.S. Pat. No. 6,501,272 is capable of bringing the signal value for the inside of a blood vessel closer to zero, but is limited in that it cannot produce a negative signal value. This technique also entails complicated processing and a decreased signal-to-noise ratio (SNR).

In the phase contrast method, magnetic resonance signals have to be collected in two sets of sequences to obtain one image. This leads to a longer imaging time. Moreover, as the phase difference is limited to 180 degrees, the velocity of a target blood flow has to be known, and it is difficult to set an appropriate imaging parameter to obtain a satisfactory image.

Under these circumstances, the present applicant has proposed, as Jpn. Pat. Appln. KOKAI Publication No. 2008-272248 (US2008/0119721), a technique for generating, on the basis of data obtained by the WB method and data obtained by the BB method, another type of data that provides a higher contrast between a tissue of interest and a background than the data obtained by the above-mentioned methods. In accordance with the principle of this technique, a signal value obtained by the BB method is subtracted from a signal value obtained by the WB method. Thus, as the difference between the signal value obtained by the WB method and the signal value obtained by the BB method is greater in a blood vessel than in a background portion, it is possible to obtain data in which the difference between the signal value of the blood vessel and the signal value of the static portion is greater than in both the data obtained by the WB method and the data obtained by the BB method.

However, in image reconstruction by MRA, information on the amplitudes of the magnetic resonance signals alone has been conventionally used. Thus, in the BB method, a thick blood vessel with a high flow velocity of blood, for example, may not be completely dephased and may be returned from a negative to a positive when the signal value of a part with a negative phase is an absolute value. In this case, the contrast rather decreases if the technique described in Jpn. Pat. Appln. KOKAI Publication No. 2008-272248 is applied.

Furthermore, when the background portion has a signal void in the BB method, the signal value of the blood vessel is higher than the signal value of the background portion due to the above-mentioned return. Thus, the contrast considerably decreases if the technique described in Jpn. Pat. Appln. KOKAI Publication No. 2008-272248 is applied.

On the other hand, a GRE sequence is generally used in the TOF method for obtaining a WB image. In the TOF method, a rephase sequence is generally used so that spins in a voxel may be in phase to produce a vector sum for maximizing a signal. The rephase sequence is normally obtained by primary gradient moment nulling (GMN). In the primary GMN, the phases of zeroeth and primary flow components that are predominant in a magnetic resonance signal should be substantially zero, thus the information on the amplitudes of the magnetic resonance signals alone has been conventionally used for image generation by the TOF method.

However, a moment of a second order or higher order is not rephased in primary GMN. Therefore, spins in a voxel are not completely in phase, and no magnetic resonance signal having the maximum amplitude component is obtained. However, in GMN, variation patterns of a gradient magnetic field pulse are more complicated and TE increases if moments of higher orders are rephased. Thus, primary GMN has heretofore been generally used as described above. A GRE sequence of zeroeth GMN may be used to further reduce the TE. In accordance with zeroeth GMN, the diffusion of phases in a voxel does not increase much and the capability of visualizing turbulent parts such as an aneurysm may be improved owing to the reduction of components of a second moment or higher order moment attributed to the TE reduction effect. However, it is pointed out that the capability of visualization in a periphery equivalent to a major arterial secondary branch or farther may decrease.

As described above, a sufficient contrast may not be obtained in the WB method as well.

The same holds true not only with blood vessel imaging but also with an imaging method that visualizes the abnormal tissue by use of the difference in susceptibility between the normal tissue and the abnormal tissue.

BRIEF SUMMARY OF EXEMPLARY EMBODIMENTS

Under the circumstances, there has been a desire for an improved contrast between a flow portion such as a blood vessel and a background portion or between parts different in susceptibility.

According to a first aspect of the present invention, there is provided a magnetic resonance imaging apparatus comprising: a detection unit that detects a magnetization vector for each of a large number of pixel positions in an imaging region including at least part of a subject, the magnetization vector being excited to have a phase difference between a flow portion in which a fluid flows and a static portion in which tissues are static or between a normal portion and an abnormal portion different in susceptibility from the normal portion; a decision unit that decides a pixel value of each pixel position as a value proportional to an absolute value of the amplitude of the magnetization vector detected for each of the large number of pixel positions; and a correction unit that corrects, on the basis of a real part or phase of the magnetization vector detected for each of the large number of pixel positions, the pixel value decided by the decision unit so that the difference of the pixel value increases between the flow portion or the abnormal portion and the static portion or the normal portion.

According to a second aspect of the present invention, there is provided a magnetic resonance imaging apparatus comprising: a first detection unit that detects a first magnetization vector for each of a large number of pixel positions in an imaging region including at least part of a subject, the first magnetization vector being excited to have a higher amplitude in a flow portion in which a fluid flows than in a static portion in which tissues are static or to have a higher amplitude in an abnormal portion different in susceptibility from a normal portion than in the normal portion and to have a phase difference between the flow portion or the abnormal portion and the static portion or the normal portion; a first generation unit that generates first data, the first data including, as a first pixel value of each pixel position, a value proportional to an absolute value of the amplitude of the first magnetization vector detected for each of the large number of pixel positions; a second detection unit that detects a second magnetization vector for each of the large number of pixel positions, the second magnetization vector being excited to have a lower amplitude in the flow portion or the abnormal portion than in the static portion or the normal portion and to have a phase difference between the flow portion or the abnormal portion and the static portion or the normal portion; a second generation unit that generates second data, the second data including, as a second pixel value of each pixel position, a value proportional to an absolute value of the amplitude of the second magnetization vector detected for each of the large number of pixel positions; a correction unit that corrects at least one of the first and second data so that the difference of the pixel value increases between the flow portion or the abnormal portion and the static portion or the normal portion, the correction unit correcting the first data on the basis of a real part or phase of the first magnetization vector detected for each of the large number of pixel positions, the correction unit correcting the second data on the basis of a real part or phase of the second magnetization vector detected for each of the large number of pixel positions; and a third generation unit that generates third data in which the contrast between the flow portion or the abnormal portion and the static portion or the normal portion is higher than in the first and second data, the third generation unit generating the third data on the basis of the first data corrected by the correction unit and the second data generated by the second generation unit when the correction unit only corrects the first data, the third generation unit generating the third data on the basis of the first data generated by the first generation unit and the second data corrected by the correction unit when the correction unit only corrects the second data, the third generation unit generating the third data on the basis of the first and second data corrected by the correction unit when the correction unit corrects both the first and second data.

According to a third aspect of the present invention, there is provided a magnetic resonance imaging apparatus comprising: a detection unit that detects, as a first echo and a second echo by a multi-echo method, a first magnetization vector and a second magnetization vector for each of a large number of pixel positions in an imaging region including at least part of a subject, the first magnetization vector being excited to have a higher amplitude in a flow portion in which a fluid flows than in a static portion in which tissues are static or to have a higher amplitude in an abnormal portion different in susceptibility from a normal portion than in the normal portion and to have a phase difference between the flow portion or the abnormal portion and the static portion or the normal portion, the second magnetization vector being excited to have a lower amplitude in the flow portion or the abnormal portion than in the static portion or the normal portion and to have a phase difference between the flow portion or the abnormal portion and the static portion or the normal portion; a unit that generates data, the data including, as a pixel value for each pixel position, a value proportional to an absolute value of the amplitude of the second magnetization vector detected as the second echo for each of the large number of pixel positions; a unit that obtains a background phase attributed to the static portion or the normal portion in the second magnetization vector for each of the large number of pixel positions on the basis of the phase of the first magnetization vector detected as the first echo; a unit that calculates a corrected phase of each pixel position as a phase in which the background phase is excluded from the phase of the second magnetization vector detected as the second echo for each of the large number of pixel positions; and a unit that corrects the pixel value of the data at the pixel position where the corrected phase calculated for each of the large number of pixel positions is not zero, the correction being made so that the difference increases between the relevant pixel value and a pixel value of the data at the pixel position where the corrected phase is zero.

According to a fourth aspect of the present invention, there is provided a magnetic resonance imaging apparatus comprising: a detection unit that detects, as a first echo and a second echo by a multi-echo method, a first magnetization vector and a second magnetization vector for each of a large number of pixel positions in an imaging region including at least part of a subject, the first magnetization vector being excited to have a higher amplitude in a flow portion in which a fluid flows than in a static portion in which tissues are static or to have a higher amplitude in an abnormal portion different in susceptibility from a normal portion than in the normal portion and to have a phase difference between the flow portion or the abnormal portion and the static portion or the normal portion, the second magnetization vector being excited to have a lower amplitude in the flow portion or the abnormal portion than in the static portion or the normal portion and to have a phase difference between the flow portion or the abnormal portion and the static portion or the normal portion; a unit that generates first data, the first data including, as a first pixel value for each pixel position, a value proportional to an absolute value of the amplitude of the first magnetization vector detected as the first echo for each of the large number of pixel positions; a unit that generates second data, the second data including, as a second pixel value for each pixel position, a value proportional to an absolute value of the amplitude of the second magnetization vector detected as the second echo for each of the large number of pixel positions; a unit that obtains a background phase attributed to the static portion or the normal portion in the second magnetization vector for each of the large number of pixel positions on the basis of the phase of the first magnetization vector; a unit that corrects the second magnetization vector detected as the second echo for each of the large number of pixel positions so that the background phase is excluded from the second magnetization vector; and a unit that generates, on the basis of the first magnetization vector and the corrected second magnetization vector, third data in which the contrast between the flow portion or the abnormal portion and the static portion or the normal portion is higher than in the first and second data.

According to a fifth aspect of the present invention, there is provided a magnetic resonance imaging apparatus comprising: a detection unit that detects a magnetization vector for each of a large number of pixel positions in an imaging region including at least part of a subject, the magnetization vector being excited to have a phase difference between a flow portion in which a fluid flows and a static portion in which tissues are static or between a normal portion and an abnormal portion different in susceptibility from the normal portion; a unit that generates an amplitude image of the subject on the basis of an amplitude component in the magnetization vector detected for each of the large number of pixel positions, a unit that obtains a real part of a background phase of the magnetization vector from a complex signal that is obtained from the magnetization vector detected for each of the large number of pixel positions, a unit that generates a cosine filter on the basis of the real part of the background phase, and a unit that applies the cosine filter to an amplitude image to obtain an image in which the real part of the background phase is corrected.

According to a sixth aspect of the present invention, there is provided a magnetic resonance imaging apparatus comprising: a unit that acquires a magnetic resonance signal related to an imaging region including a blood vessel portion and a static portion of a subject by a pulse sequence, the pulse sequence including a dephase gradient magnetic field pulse to enhance a signal decrease in the blood vessel portion more than in the static portion; a unit that modifies the phase of the magnetic resonance signal of the imaging region so that the phase of the magnetic resonance signal of the static portion is zero and so that the phase of the magnetic resonance signal of the blood vessel portion is closer to ±180 degrees; and a unit that generates an image of a blood vessel in the imaging region on the basis of the magnetic resonance signal in which the phase is modified.

According to a seventh aspect of the present invention, there is provided a magnetic resonance imaging apparatus comprising: a unit that acquires a magnetic resonance signal related to an imaging region including a blood vessel portion and a static portion of a subject by a pulse sequence, the pulse sequence including a dephase gradient magnetic field pulse to enhance a signal decrease in the blood vessel portion more than in the static portion; a unit that generates a real image and an imaginary image on the basis of the magnetic resonance signal of the imaging region; a unit that generates an intensity image and a phase image on the basis of the real image and the imaginary image; a unit that generates, on the basis of the phase image, a modified phase image in that the weight of a portion having no (zero) phase change is plus 1 and in which the weight of a portion having a reverse phase (±180 degrees) is minus 1; and a unit that applies the modified phase image to the intensity image.

According to an eighth aspect of the present invention, there is provided a magnetic resonance imaging apparatus comprising: a detection unit that detects a magnetization vector for each of a large number of pixel positions in an imaging region including at least part of a subject by using of a time of flight (TOF) method, the magnetization vector being excited to have a phase difference between a flow portion in which a fluid flows and a static portion in which tissues are static; a unit that generates an amplitude image of the subject on the basis of an amplitude component in the magnetization vector detected for each of the large number of pixel positions, a unit that obtains a real part of a background phase of the magnetization vector from a complex signal that is obtained from the magnetization vector detected for each of the large number of pixel positions, a unit that generates a cosine filter on the basis of the real part of the background phase, and a unit that applies the cosine filter to an amplitude image to obtain an image in which the real part of the background phase is corrected.

Additional objects and advantages of the invention will be set forth in the description that follows, and in part will be obvious from the description, or may be learned by practice of the exemplary embodiments. The objects and advantages hereof may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention and, together with the general description given above and the detailed description of the embodiments given below, serve to explain the principles of the exemplary embodiments.

FIG. 1 is a diagram showing the schematic configuration of a magnetic resonance imaging apparatus (MRI apparatus) according to one embodiment of the present invention;

FIG. 2 is a flowchart showing a procedure for operating the MRI apparatus shown in FIG. 1 to obtain hybrid MRA in a first embodiment;

FIG. 18 is a graph showing the distribution of a phase $\phi2_{cor}$;

FIG. 19 is a graph showing one example of the window function W;

FIG. 20 is a graph showing one example of the distribution of an enhanced phase $\phi_{cor.enh}$;

FIG. 21 is a graph showing one example of the relation among a vector $V2_{cor.enh}$ associated with a vector $V2_{cor}$ shown in FIG. 14, a vector difference $V1-V2_{cor.enh}$ and a real part $A1-Re[V2_{cor.enh}]$;

FIG. 22 is a graph showing by comparison a vector for TOF and vectors for FS-BB before and after correction for a blood vessel located on the left in FIG. 16;

FIG. 23 is a graph showing by comparison a vector for TOF and vectors for FS-BB before and after correction for a blood vessel located on the right in FIG. 16;

FIG. 26 is a graph showing the distribution of a conventional image value obtained as the difference between TOF and FS-BB shown in FIG. 16;

FIG. 27 is a flowchart showing a processing procedure in correcting a BB image by the computation unit in FIG. 1 in a third embodiment;

FIG. 29 is a view showing a real part image obtained by a conventional FS-BB method and a real part image obtained by the third embodiment;

DETAILED DESCRIPTION OF EXEMPLARY EMBODIMENTS

Figure 3:
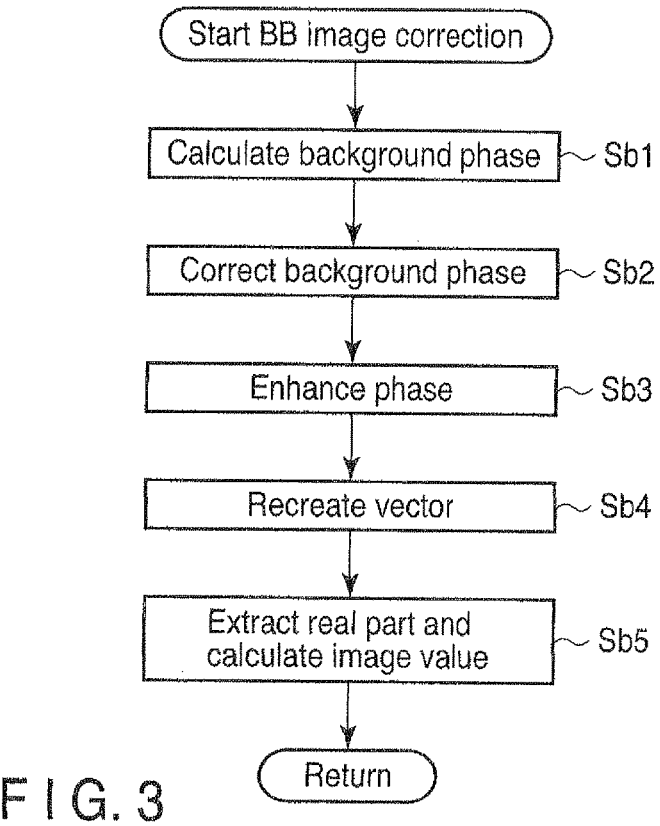
FIG. 3 is a flowchart showing a processing procedure in correcting a BB image by a computation unit in FIG. 1.

Exemplary embodiments of the present invention will be hereinafter described with reference to the drawings.

FIG. 1 is a diagram showing the schematic configuration of a magnetic resonance imaging apparatus (MRI apparatus) 100 according to the present embodiments.

The MRI apparatus 100 comprises a bed unit, a static-magnetic-field generating unit, a gradient-magnetic-field generating unit, a receiving/transmitting unit, and a control/operating unit. The bed unit moves a subject 200 mounted thereon. The static-magnetic-field generating unit generates a static magnetic field. The gradient-magnetic-field generating unit generates a gradient magnetic field designed to add position information to the static magnetic field. The receiving/transmitting unit receives and transmits a radio-frequency signal. The control/operating unit controls the whole system and reconstructs images. The MRI apparatus 100 has, as components of these units, a magnet 1, a static magnetic power supply 2, a shim coil 3, a shim power supply 4, a top plate 5, a gradient coil unit 6, a gradient power supply 7, an RF coil unit 8, a transmitter 9T, a receiver 9R, a sequencer (sequence controller) 10, a computation unit 11, a storage unit 12, a display 13, an input device 14, a sound generator 15, and a host computer 16. Connected to the MRI apparatus 100 is an electrocardiograph unit that measures an ECG signal as a signal representing the cardiac pulsation of the subject 200.

The static-magnetic-field generating unit includes the magnet 1, the static magnetic power supply 2, the shim coil 3 and the shim power supply 4. For example, a superconducting magnet or a normal conducting magnet can be used as the magnet 1. The static magnetic power supply 2 supplies a current to the magnet 1. In addition, the static magnetic power supply 2 can be omitted when the superconducting magnet is employed as the magnet 1. The static-magnetic-field generating unit therefore generates a static magnetic field $B_0$ in a cylindrical space (diagnostic space) into which the subject 200 is moved. The direction of the static magnetic field $B_0$ virtually coincides with the axial direction (Z-axis direction) of the diagnostic space. The shim coil 3 generates a correction magnetic field for rendering the static magnetic field uniform when a current is supplied to it from the shim power supply 4 under the control of the host computer 16.

The bed unit moves the top plate 5, on which the subject 200 is lying, into or out of the diagnostic space.

The gradient-magnetic-field generating unit includes the gradient coil unit 6 and the gradient power supply 7. The gradient coil unit 6 is arranged in the magnet 1. The gradient coil unit 6 has three coils 6x, 6y and 6z that generate gradient magnetic fields extending in mutually orthogonal X-, Y- and Z-axes, respectively. The gradient power supply 7 supplies pulse currents for generating gradient magnetic fields to the coils 6x, 6y and 6z, under the control of the sequencer 10. The gradient-magnetic-field generating unit controls the pulse currents supplied from the gradient power supply 7 to the coils 6x, 6y and 6z. Thus, the gradient-magnetic-field generating unit synthesizes gradient magnetic fields extending in the three physical axes (the X-, Y- and Z-axes), respectively. The unit sets these magnetic fields in logical axes defined by a slice direction gradient magnetic field Gs, a phase-encode direction gradient magnetic field Ge and a read-out direction (frequency-encode) gradient magnetic field Gro, respectively, which intersect at right angles with one another. The slice, phase-encode and read-out direction gradient magnetic fields, Gs, Ge and Gr are superposed on the static magnetic field $B_0$.

The receiving/transmitting unit includes the RF coil unit 8, the transmitter 9T, and the receiver 9R. The RF coil unit 8 is arranged in the vicinity of the subject 200 in the diagnostic space. The transmitter 9T and the receiver 9R are connected to the RF coil unit 8. The transmitter 9T and the receiver 9R operate under the control of the sequencer 10. The transmitter 9T supplies an RF current pulse of Larmor frequency to the RF coil unit 8 in order to induce nuclear magnetic resonance (NMR). The receiver 9R acquires an MR signal (radio-frequency signal), such as an eco signal, which the RF coil unit 8 has received. The receiver 9R then performs, on the MR signal, various processes, such as pre-amplification, intermediate-frequency conversion, phase detecting, low-frequency amplification and filtering. Finally, the receiver 9R performs analog-to-digital (A/D) conversion on the MR signal, producing digital data (raw data).

The control/operating unit includes the sequencer 10, the computation unit 11, the storage unit 12, the display 13, the input device 14, the sound generator 15 and the host computer 16.

The sequencer 10 has a CPU and a memory. The sequencer 10 stores, into the memory, pulse sequence information transmitted from the host computer 16. The CPU of the sequencer 10 controls the operations of the gradient power supply 7, transmitter 9T and receiver 9R in accordance with the sequence information stored in the memory. The CPU of the sequencer 10 also receives the raw data output from the receiver 9R and transfers the raw data to the computation unit 11. Note that the sequence information is all data necessary for operating the gradient power supply 7, transmitter 9T and receiver 9R in accordance with the pulse sequence. It includes, for example, information about the intensity of the pulse current supplied to the coils 6x, 6y and 6z, the period of applying the pulse current and the timing of applying the pulse current.

The computation unit 11 receives the raw data output from the transmitter 9T, through the sequencer 10. The computation unit 11 has an internal memory. The internal memory has a k-space (also called Fourier space or frequency space), in which the raw data input to the computation unit 11 is placed. The computation unit 11 subjects the data placed in the k-space to two- or three-dimensional Fourier transform, thereby reconstructing video data for the real space. The computation unit 11 can perform, if necessary, synthesis and differential operations (including weighted differentiation) on any data representing an image. The synthesis includes cumulative addition of pixel values, maximum intensity projection (MIP), minimum intensity projection (minIP), and the like. As another example of the synthesis, the axes of several frames may be aligned in a Fourier space, and the raw data items representing these frames may be synthesized, thereby generating one-frame raw data. The addition of pixel values includes, for example, simple addition, addition averaging or weighting addition.

The storage unit 12 stores video data reconstructed or video data subjected to the above-mentioned synthesis or differential processing.

The display 13 displays various images to be presented to a user, under the control of the host computer 16. For example, a display device such as a liquid crystal display can be used as the display 13.

The input device 14 is operated to input various types of information, such as parameter information for selecting synchronization timing desired by the operator, scanning conditions, the pulse sequence, information about the image synthesis and differential operation, and the like. The input device 14 sends the input information to the host computer 16. The input device 14 comprises, as the case may be, a pointing device such as a mouse or a track ball, a selection device such as a mode change switch, or an input device such as keyboard.

The sound generator 15 generates messages for the start and end of breath holding as sounds when instructed by the host computer 16.

The host computer 16 controls the operation of every unit of the MRI apparatus 100 to achieve various operations achieved by existing MRI apparatuses. The host computer 16 additionally has a function to set a scaling factor when hybrid MRA is performed as described later.

The electrocardiograph unit includes an ECG sensor 17 and an ECG unit 18. The ECG sensor 17 is attached to the surface of the body of the subject 200, and detects an ECG signal of the subject 200 as an electric signal (hereinafter referred to as a sensor signal). The ECG unit 18 subjects the sensor signal to various kinds of processing, including digitization, and then outputs it to the host computer 16 and the sequencer 10. For example, a vector electrocardiograph can be used as the electrocardiograph unit. The sequencer 10 uses the sensor signal generated by the electrocardiograph unit, when it is necessary to carry out a scan in synchronization with the cardiac phase of the subject 200.

The operation of the MRI apparatus 100 configured as described above will next be described. It is to be noted that the MRI apparatus 100 can perform various kinds of imaging achieved by existing MRI apparatuses that are, however, not described. Here, operations in the case of obtaining hybrid MRA are explained. Here, first and second embodiments that are different in the processing for obtaining the hybrid MRA are described in detail.

(First Embodiment)

FIG. 2 is a flowchart showing a procedure for operating the MRI apparatus to obtain hybrid MRA in the first embodiment.

In step Sa1, the sequencer 10 controls the gradient power supply 7, the transmitter 9T and the receiver 9R to collect data in both a WB method and a BB method. The data collection in the WB method and the data collection in the BB method may be carried out in separate sequences, but a multi-echo method is used here to carry out the data collection in both the WB method and the BB method in a series of sequences. The data collection is carried out for each of a plurality of slices in a slab set as an imaging region.

Any methods may be specifically employed as the WB method and the BB method. However, here, a TOF method is used as the WB method, and a flow-sensitive BB (FS-BB) method is used as the BB method. In addition, the FS-BB carries out data collection in a pulse sequence based on a gradient echo including a dephase gradient magnetic field pulse for enhancing a signal decrease due to flows in arteries and veins in a region of interest.

In step Sa2, the computation unit 11 reconstructs an image in which blood vessels are indicated at higher signal intensity than the background (hereinafter referred to as a WB image) on the basis of the data collected by use of the TOF method as described above. The computation unit 11 also reconstructs an image in which blood vessels are indicated at lower signal intensity than the background (hereinafter referred to as a BB image) on the basis of the data collected by use of the FS-BB method as described above.

In step Sa3, the computation unit 11 corrects the BB image using phase information. FIG. 3 is a flowchart showing a processing procedure in correcting the BB image by the computation unit 11.

First, a vector V is represented by the following equation:

$$V = A\exp[j\phi]$$

wherein V indicates a vector of a complex component of the magnetization that has generated a magnetic resonance signal acquired by the FS-BB method, A indicates the amplitude, and $\phi$ indicates the phase.

Here, a phase $\phi_{flow}$ attributed to flow is added to a static portion phase (background phase) $\phi_{back}$ in the vector V. The static portion phase varies depending on TE. That is, the phase $\phi$ is determined by the following equation:

$$\phi = \phi_{flow} + \phi_{back}$$

In step Sb1, the computation unit 11 calculates a phase $\phi_{low}$ by a low pass filter $H_{low}$ of appropriate intensity:

$$\phi_{low} = \arg[H_{low}[V]].$$

Then, this phase $\phi_{low}$ is approximately equal to the background phase.

That is, $\phi_{low} \approx \phi_{back}$.

In step Sb2, the computation unit 11 obtains a vector $V_{cor}$ from which the influence of the background phase $\phi_{back}$ is excluded, by the following equation:

$$V_{cor} = V\exp[-j\phi_{back}]$$

That is, a phase $\phi_{cor}$ in which the influence of the background phase $\phi_{back}$ is excluded from the phase $\phi$ is represented by the following equation:

$$\phi_{cor} = \arg[V_{cor}].$$

The phase $\phi_{cor}$ after the correction of the background phase only has the phase $\phi_{flow}$ attributed to flow if TE is sufficiently short or if a low-frequency phase is predominant in a phase attributed to the non-uniformity of a magnetic field. That is, the following equation is satisfied:

$$\phi_{cor} \approx \phi_{flow}$$

wherein $\phi_{flow}$ is indefinite due to the flow velocity and direction.

Figure 4:
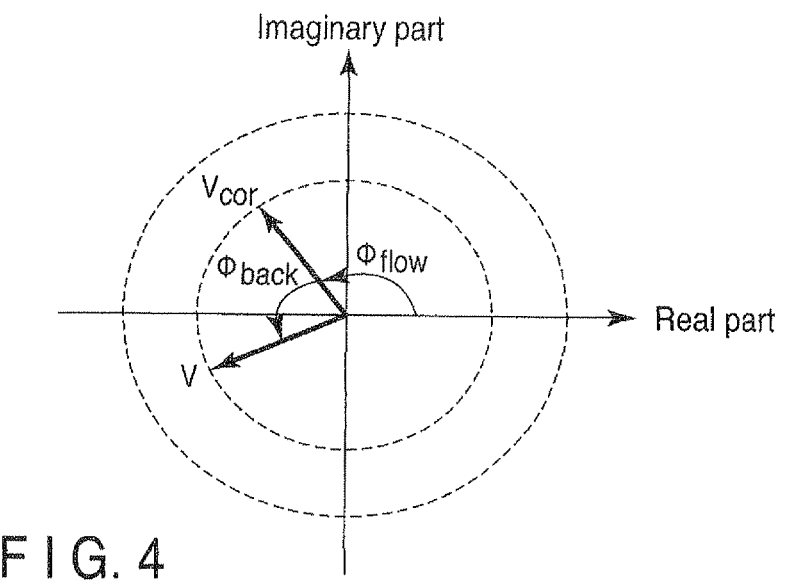
FIG. 4 is a graph showing one example of the relation among a vector V, a vector $V_{co1}$, a phase $\phi_{flow}$ and a phase $\phi_{back}$.

FIG. 4 is a graph showing one example of the relation among the vector V, a vector $V_{co1}$, the phase $\phi_{flow}$ and the phase $\phi_{back}$.

Figure 5:
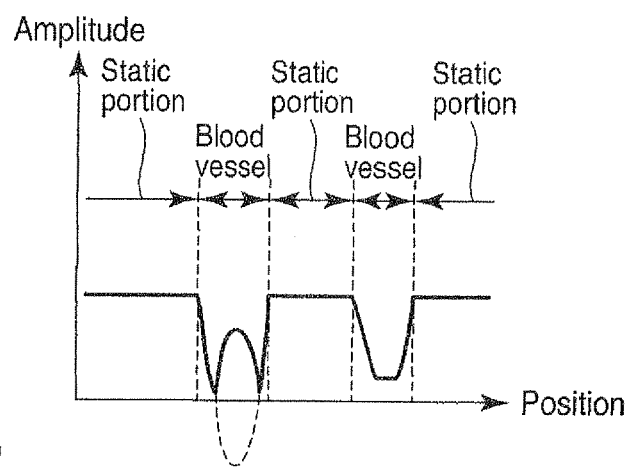
FIG. 5 is a graph showing one example of the distribution of amplitudes in BB image.

FIG. 5 is a graph showing one example of the distribution of amplitudes in the BB image. FIG. 5 shows the amplitudes of magnetic resonance signals collected from positions on a straight line that passes through a blood vessel at two points. As this is based on BB, amplitude is lower in the blood vessel than in a background portion. However, the signal value of the blood vessel on the left in FIG. 5 is returned from a negative to a positive.

Figure 6:
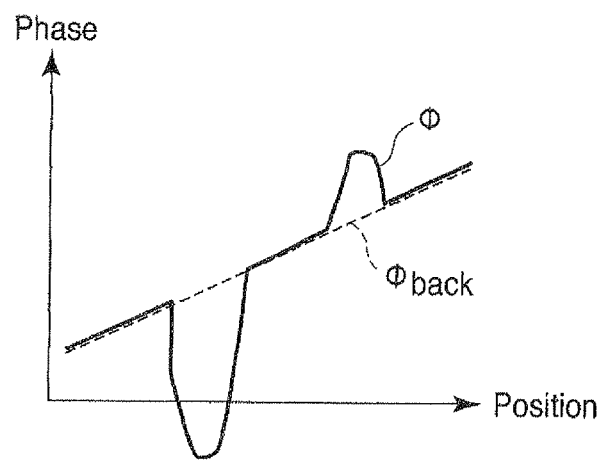
FIG. 6 is a graph showing one example of the distribution of phases on the same straight line on which the distribution of the amplitudes is shown in FIG. 5.

FIG. 6 is a graph showing one example of the distribution of phases on the same straight line on which the distribution of the amplitudes is shown in FIG. 5. In FIG. 6, the phase $\phi$ is indicated by a thick full line, and the background phase $\phi_{back}$ is indicated by a dashed-dotted line.

Figure 7:
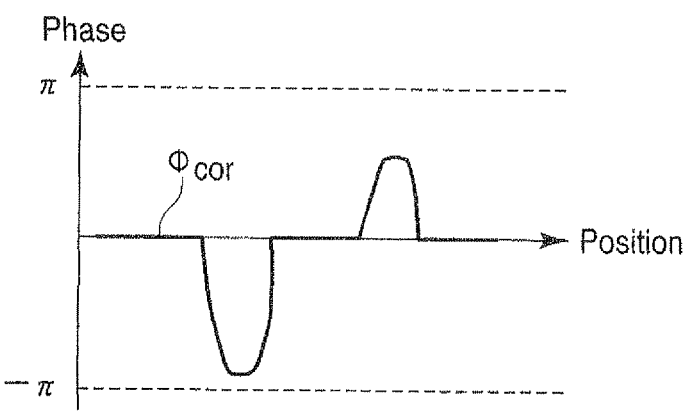
FIG. 7 is a graph showing the distribution of a phase $\phi_{cor}$.

FIG. 7 is a graph showing the distribution of the phase $\phi_{cor}$.

This phase $\phi_{cor}$ is other than zero at the position corresponding to the blood vessel, and is zero at the position corresponding to the static portion.

Figure 8:
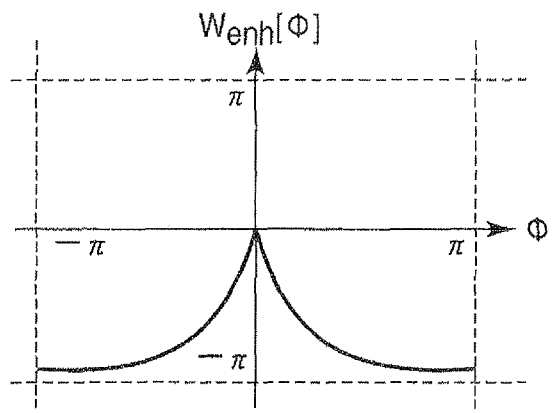
FIG. 8 is a graph showing one example of a window function W.

In step Sb3, the computation unit 11 enhances the phases so that the phase of the blood vessel may be closer to ±180° while the phase of the background portion may remain zero. That is, in order to increase the contrast of the BB image, the real part of the vector $V_{cor}$ is positively or negatively increased only for the blood vessel in accordance with the phase of the vector $V_{cor}$ while the static portion is kept at zero. Specifically, for example, a window function W as shown in FIG. 8 is prepared, and the phase $V_{cor}$ is converted into an enhanced phase $\phi_{cor.enh}$ by the following equation:

$$\phi_{cor.enh} = W_{enh}[V_{cor}].$$

Figure 9:
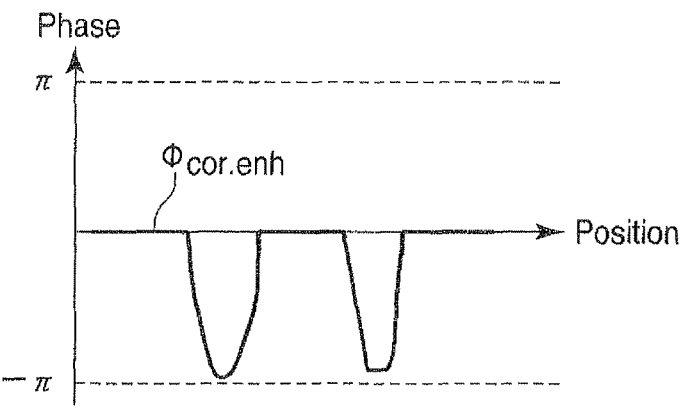
FIG. 9 is a graph showing one example of the distribution of an enhanced phase $\phi_{cor.enh}$.

FIG. 9 is a graph showing one example of the distribution of the enhanced phase $\phi_{cor.enh}$.

In step Sb4, the computation unit 11 creates (recreates) a vector $V_{cor.enh}$ in the enhanced phase $\phi_{cor.enh}$ by the following equation:

$$V_{cor.enh} = \text{abs}[V]\exp[j\phi_{cor.enh}].$$

In step Sb5, the computation unit 11 extracts a real part $\text{Re}[V_{cor.enh}]$ of the vector $V_{cor.enh}$, and uses this real part as a signal value I of the corrected BB image. That is, the signal value I is found by the following equation:

$$I = \text{Re}[V_{cor.enh}].$$

Figure 10:
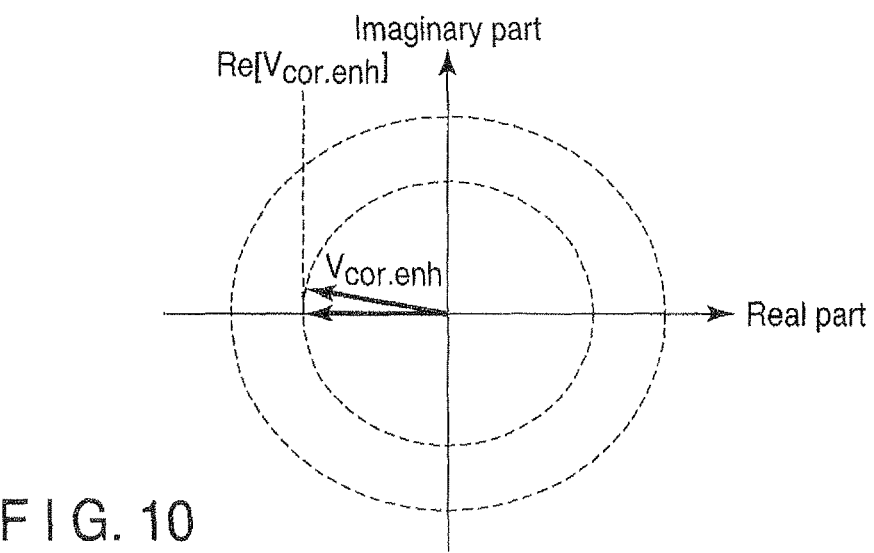
FIG. 10 is a graph showing one example of the relation between a vector $V_{cor.enh}$ obtained for a vector $V_{cor}$ shown in FIG. 4 and a real part $Re[V_{cor.enh}]$.

FIG. 10 is a graph showing one example of the relation between the vector $V_{cor.enh}$ obtained for the vector $V_{cor}$ shown in FIG. 4 and the real part $\text{Re}[V_{cor.enh}]$.

Figure 11:
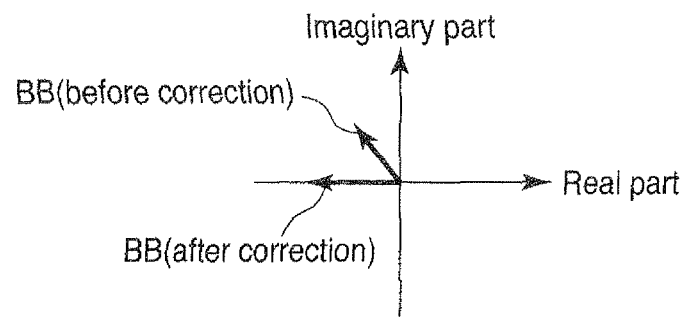
FIG. 11 is a graph showing by comparison vectors before and after correction for a blood vessel located on the left in FIG. 5.

FIG. 11 is a graph showing by comparison vectors before and after correction for the blood vessel located on the left in FIG. 5.

Figure 12:
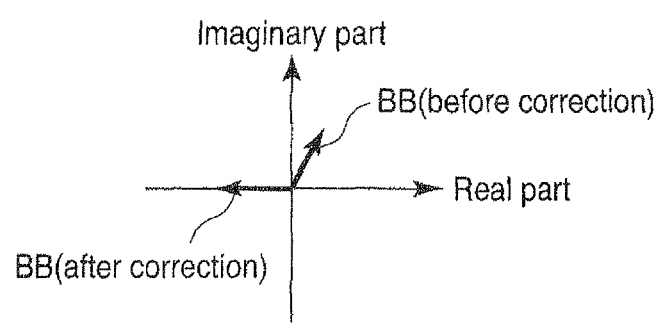
FIG. 12 is a graph showing by comparison vectors before and after correction for a blood vessel located on the right in FIG. 5.

FIG. 12 is a graph showing by comparison vectors before and after correction for the blood vessel located on the right in FIG. 5.

Figure 13:
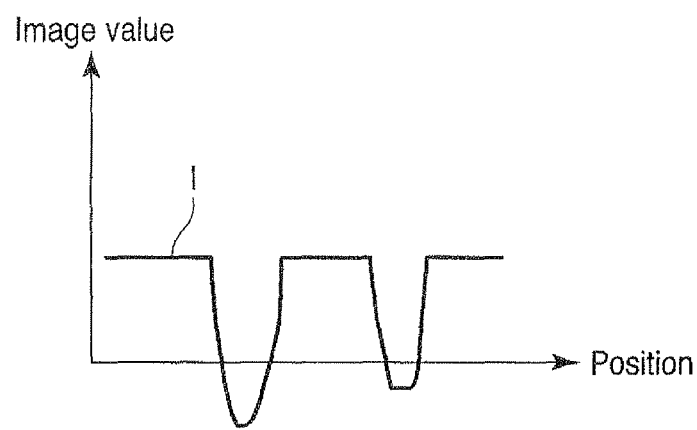
FIG. 13 is a graph showing one example of the distribution of a signal value I obtained by the above-mentioned correction for the positions on the straight line having the distribution of amplitudes and phases shown in FIGS. 5 and 6.

FIG. 13 is a graph showing one example of the distribution of the signal value I obtained by the above-mentioned correction for the positions on the straight line having the distribution of amplitudes and phases shown in FIGS. 5 and 6.

A pixel value I thus obtained has an increased difference between a pixel value determined for a position corresponding to the blood vessel in the original BB image and a pixel value determined for a position corresponding to the static portion. Thus, the BB image is corrected so that the contrast of the blood vessel to the background portion may be increased. Therefore, the BB image thus corrected more accurately visualizes the form of the blood vessel than the BB image before corrected.

Furthermore, a hybrid MRA image higher in the accuracy of blood vessel visualization than heretofore can be obtained by the following processing using the BB image corrected as described above.

After the above-described correction has been finished, the flow moves from step Sa3 to step Sa4 in FIG. 2 if necessary. In step Sa4, the computation unit 11 generates a hybrid MRA image by calculating a scaling difference between the WB image and the BB image. That is, a difference value ΔS is calculated by Equation (1) below:

$$\Delta S = S(WB) - \alpha \times S(BB) \quad (1)$$

wherein S(WB) is a signal value in the WB image for each of the pixels associated with the same position, S(BB) is a signal value in the BB image after the above-mentioned correction, and α is a scaling factor.

The signal value S(WB) in the WB image is higher than a signal value Sbase(WB) of a background portion regarding the blood vessel. The signal value S(BB) in the BB image is lower than a signal value Sbase(BB) of the background portion regarding the blood vessel.

Thus, the difference value ΔS is higher than both the signal value S(WB) and the signal value S(BB). As a result, the contrast of the blood vessel to the background portion is higher than in both the WB image and the BB image.

Then, the hybrid MRA images mentioned above are generated for all the slices in the slab.

On the other hand, in step Sa5, the computation unit 11 generates a mask image on the basis of the WB image. This mask image is an image representing a region corresponding to a cerebral parenchyma when it images, for example, blood vessels in a brain. It is difficult to extract the region of the cerebral parenchyma from the BB image because, for example, a signal difference between the cerebral parenchyma and its peripheral parts is small in the BB image. However, the cerebral parenchyma and the blood vessels have high signal intensity in the WB image, so that the regions of the cerebral parenchyma and the blood vessels can be extracted from the WB image by simple processing such as threshold processing.

In step Sa6, the computation unit 11 performs MIP processing for a plurality of hybrid MRA images to generate a hybrid MRA MIP image. The hybrid MRA images targeted for the MIP processing may be all or some of the hybrid MRA images for all the slices, or a plurality of hybrid MRA images generated by reformation. Moreover, this MIP processing may be only targeted for the region corresponding to the cerebral parenchyma and performed referring to the mask image generated in step Say. In addition, when another image such as a minIP image of the BB image is displayed together with the hybrid MRA MIP image, the mask image may also be referred to for minIP processing performed for this image.

As described above, according to the operation of the MRI apparatus 100 in the first embodiment, the BB image in which the return of the amplitude shown in FIG. 5 is eliminated, as is apparent from FIG. 13, is used to generate the hybrid MRA image and the hybrid MRA MIP image. Thus, the contrast of the blood vessel to the background portion can be further increased than in the case where the BB image in which the return of the amplitude shown in FIG. 5 is generated is used as it is.

(Second Embodiment)

A procedure for operating the MRI apparatus 100 to obtain hybrid MRA in the second embodiment is similar to the procedure in the first embodiment shown in FIG. 2. The second embodiment is different from the first embodiment in the specifics of the correction of the BB image in step Sa3 and the calculation of the scaling difference in step Sa4. Accordingly, this difference is described in detail below, and the operation similar to that in the first embodiment is not described.

The second embodiment is suitable for the collection of signals in the WB method and the BB method using the multi-echo method. Here, the TOF method is used for a first echo, and the FS-BB method to which a motion probing gradient (MPG) is added is used for a second echo. Moreover, water and fat have the same phase, for example, in-phase in these echoes.

First, vectors V1, V2 are represented by the following equations:

$$V1 = A1 \exp[j\phi 1]$$

$$V2 = A2 \exp[j\phi 2]$$

wherein V1 indicates a vector of a complex component of the magnetization for the first echo, A1 indicates the amplitude, and φ1 indicates the phase, while V2 indicates a vector of a complex component of the magnetization for the first echo, A2 indicates the amplitude, and φ2 indicates the phase.

Figure 14:
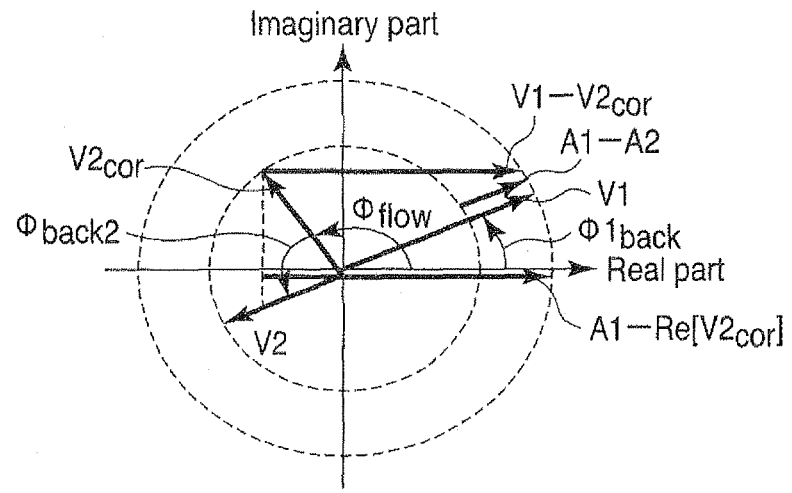
FIG. 14 is a graph showing the relation between a magnetization vector of a first echo and a magnetization vector of a second echo.

Here, in the first echo, the phase of the static portion only remains if the GMN is complete. In the second echo, the phase attributed to flow is added to the phase of the static portion. Moreover, the phase of the static portion varies depending on TE. The first echo is higher in amplitude than the second echo. Thus, as shown in FIG. 14, the following relation is satisfied:

$$\phi 1 = \phi 1_{back}$$

$$\phi 2 = \phi 2_{flow} + \phi 2_{back}$$

$$A1 \geq A2$$

Figure 15:
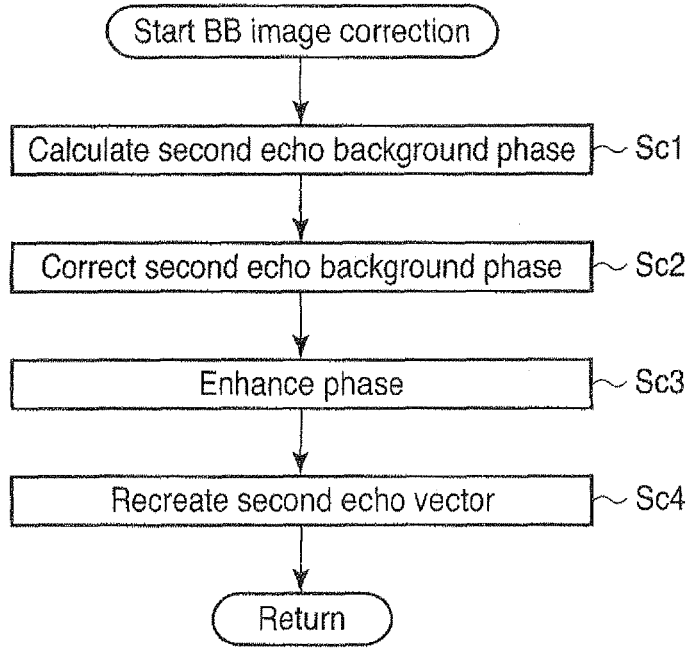
FIG. 15 is a flowchart showing a processing procedure in correcting the BB image by the computation unit in FIG. 1.

FIG. 15 is a flowchart showing a processing procedure in correcting the BB image by the computation unit 11.

In step Sc1, the computation unit 11 calculates a background phase $\phi 2_{back}$ of the second echo.

Here, if a Maxwell term is negligible, the phase of the static portion is proportional to TE in the case of a GRE sequence. Therefore, the background phase $\phi 2_{back}$ can be found by the following equation:

$$\phi 2_{back} = (TE2/TE1)\phi 1_{back} = (TE2/TE1)\phi 1$$

That is, the phase of the static portion in the second echo can be represented by using that in the first echo.

Figure 16:
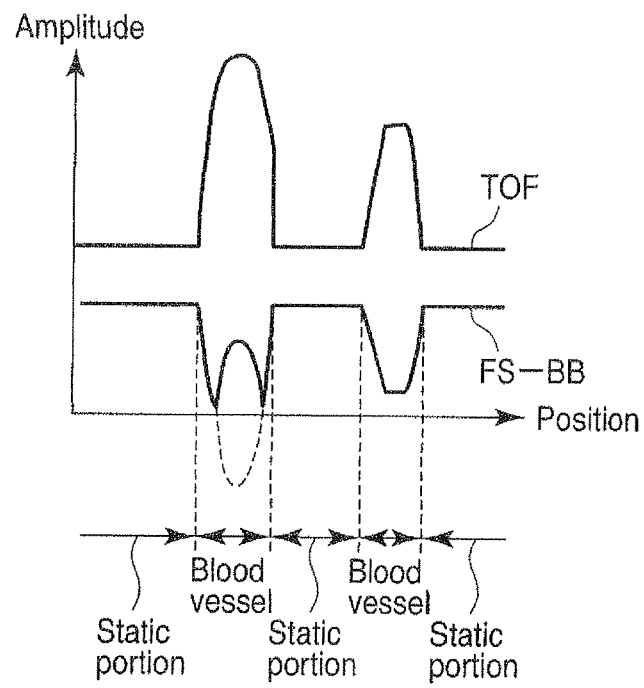
FIG. 16 is a graph showing one example of the distribution of amplitudes in TOF and FS-BB.

FIG. 16 is a graph showing one example of the distribution of amplitudes in the TOF and FS-BB. FIG. 16 shows the amplitudes of magnetic resonance signals collected from positions on a straight line that passes through a blood vessel at two points. As the TOF is a WB method, amplitude is higher in the blood vessel than in a background portion. As the FS-BB is a BB method, amplitude is lower in the blood vessel than in a background portion. However, in the FS-BB, the signal value of the blood vessel on the left in FIG. 16 is returned from a negative to a positive.

Figure 17:
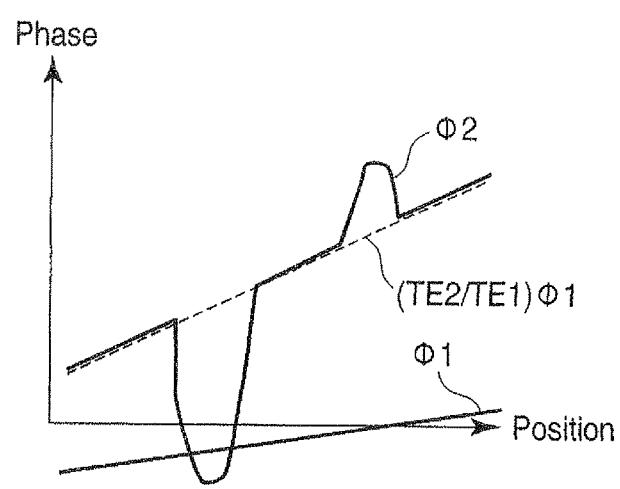
FIG. 17 is a graph showing one example of the distribution of phases on the same straight line on which the distribution of the amplitudes is shown in FIG. 16.

FIG. 17 is a graph showing one example of the distribution of phases on the same straight line on which the distribution of the amplitudes is shown in FIG. 16. In FIG. 17, the phases $\phi 1$, $\phi 2$ are indicated by full lines, and the background phase $\phi 2_{back}=(TE2/TE1)\phi 1$ in FS-BB is indicated by a dashed line.

In step Sc2, the computation unit 11 corrects the background phase in the second echo. That is, the computation unit 11 obtains a vector $V2_{cor}$ in which the influence of a background phase $\phi 2_{back}$ is excluded from the vector V2, in accordance with the following equation:

$$V2_{cor} = V2 \exp[-j\phi 2_{back}]$$
$$= A2 \exp[-j(\phi 2_{flow} + \phi 2_{back} - \phi 2_{back})]$$
$$= A2 \exp[-j\phi 2_{flow}].$$

That is, the phase $\phi 2_{cor}$ of the second echo after the correction of the background phase only includes a phase attributed to flow as in the following equation:

$$\phi 2_{cor} = \arg[V2_{cor}] \approx \phi 2_{flow}$$

The phase $\phi 2_{cor}$ is indefinite due to the flow velocity and direction. However, there is a low probability that the phase $\phi 2_{flow}$ is the same as the phase of the first echo. When a value $A_h$ of the hybrid MRA image to be found from the vectors V1, V2 is A1-A2, the value $A_h$ is equivalent to a difference, which means that the vectors V1, V2 are in phase. Therefore, even if the image value $A_h$ is defined as the absolute value of the complex component at this stage as in the following equation, a blood vessel CNR is equal to or more than at least the absolute value difference.

$$A_h = \text{abs}[V1 - V2_{cor}]$$

Alternatively, even if the difference between the amplitude of the first echo and a real part component after the correction of the background portion in the second echo is defined as in the following equation, the blood vessel CNR is still equal to or more than at least the absolute value difference.

$$A_h = A1 - Re[V2_{cor}]$$

In addition, in step Sc1 and step Sc2, the computation unit 11 may calculate from the BB image alone as in step Sb1 and step Sb2 in the first embodiment.

FIG. 18 is a graph showing the distribution of the phase $\phi 2_{cor}$.

In step Sc3, the computation unit 11 enhances the phases so that the phase of the blood vessel may be closer to ±180° while the phase of the background portion may remain zero. That is, in order to increase a blood vessel signal after the difference is obtained, the real part of the vector $V2_{cor}$ is positively or negatively increased only for the blood vessel in accordance with the phase of $V2_{cor}$ while the static portion is kept at zero. Specifically, for example, a window function W as shown in FIG. 19 is prepared, and the phase $\phi 2_{cor}$ is converted into an enhanced phase $\phi 2_{cor.enh}$ by the following equation:

$$\phi 2_{cor.enh} = W[\phi 2_{cor}].$$

FIG. 20 is a graph showing one example of the distribution of the enhanced phase $\phi_{cor.enh}$.

In step Sc4, the computation unit 11 creates (recreates) a vector $V2_{cor.enh}$ in the enhanced phase $\phi 2_{cor.enh}$ by the following equation:

$$V2_{cor.enh} = \text{Abs}[V2]\exp[j\phi 2_{cor.enh}].$$

FIG. 21 is a graph showing one example of the relation among the vector $V2_{cor.enh}$ associated with the vector $V2_{cor}$ shown in FIG. 14, a vector difference $V1 - V2_{cor.enh}$ and a real part $A1 - Re[V2_{cor.enh}]$.

FIG. 22 is a graph showing by comparison a vector for TOF and vectors for FS-BB before and after correction for the blood vessel located on the left in FIG. 16.

FIG. 23 is a graph showing by comparison a vector for TOF and vectors for FS-BB before and after correction for the blood vessel located on the right in FIG. 16.

Figure 24:
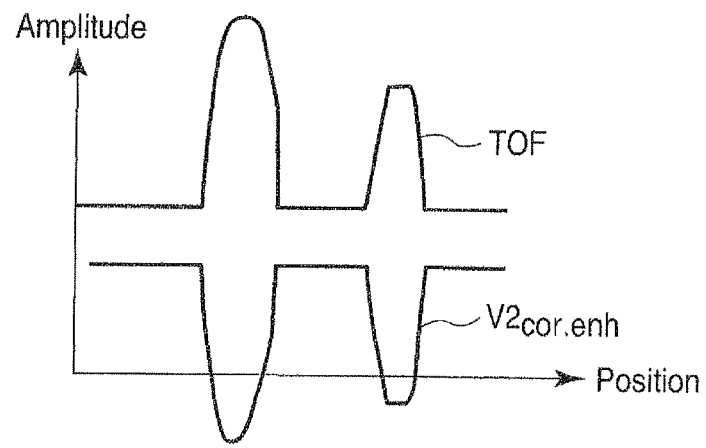
FIG. 24 is a graph showing by comparison the distribution of amplitudes in TOF shown in FIG. 16 and the distribution of amplitudes of $V2_{cor.enh}$.

FIG. 24 is a graph showing by comparison the distribution of amplitudes in TOF shown in FIG. 16 and the distribution of amplitudes of $V2_{cor.enh}$.

After the above-described correction has been finished, the flow moves from step Sa3 to step Sa4 in FIG. 2. In step Sa4, the computation unit 11 generates a hybrid MRA image by calculating a scaling difference between the WB image and the BB image. However, as the phases have been enhanced in step Sc3 so that the phase $V2_{cor.enh}$ of the second echo may be closer to −180°, no complex difference is used here, and the image value $A_h$ is found by the following equation:

$$A_h = \text{Abs}[V1] - \alpha \times Re[V2_{cor.enh}].$$

Figure 25:
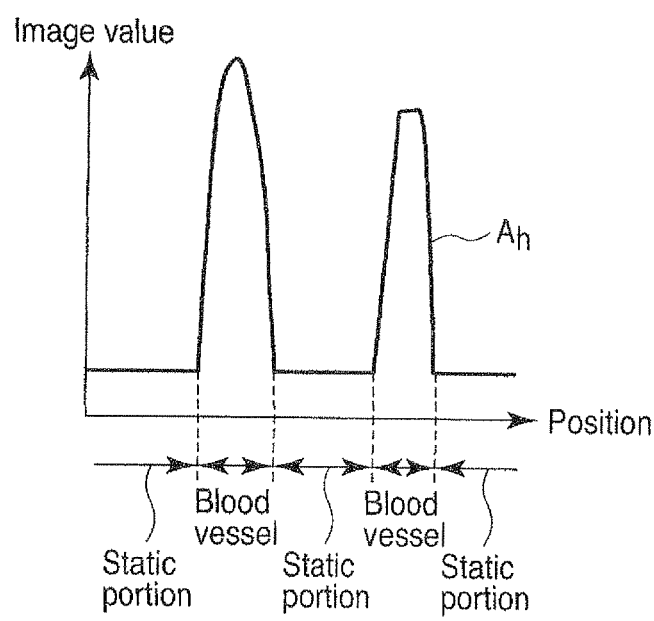
FIG. 25 is a graph showing the distribution of an image value $A_{l_1}$ obtained for TOF and $V2_{cor.enh}$ shown in FIG. 24.

FIG. 25 is a graph showing the distribution of an image value $A_h$ obtained for TOF and $V2_{cor.enh}$ shown in FIG. 24.

FIG. 26 is a graph showing the distribution of a conventional image value obtained as the difference between TOF and FS-BB shown in FIG. 16.

As described above, according to the operation of the MRI apparatus 100 in the second embodiment, the BB image in which the return of the amplitude shown in FIG. 16 is eliminated, as is apparent from FIG. 24, is used to generate the hybrid MRA image and the hybrid MRA MIP image. Thus, as is apparent from the comparison between FIG. 25 and FIG. 26, the contrast of the blood vessel to the background portion can be further increased than in the case where the BB image in which the return of the amplitude shown in FIG. 16 is generated is used as-is.

(Third Embodiment)

A procedure for operating the MRI apparatus 100 to obtain hybrid MRA in the third embodiment is similar to the procedure in the first embodiment shown in FIG. 2. The third embodiment is different from the first embodiment in the specifics of the correction of the BB image in step Sa3. Accordingly, this difference is described in detail below, and the operation similar to that in the first embodiment is not described.

FIG. 27 is a flowchart showing a processing procedure in correcting the BB image by the computation unit 11 in the third embodiment.

In step Sd1, the computation unit 11 obtains a complex signal $S_{cor}$ in which the background phase is corrected, by the following equation:

$$S_{cor} = S_{orig} \times S_{low}^* / |S_{low}|$$

wherein $S_{orig}$ is an original complex signal, $S_{low}$ is a complex signal obtained by filtering $S_{orig}$ with a low pass filter $H_{low}$, and $S_{low}*$ is a complex conjugate of the complex signal $S_{low}$.

In step Sd2, the computation unit 11 obtains a normalized real part signal $\cos(\phi_{cor})$ that is obtained after correcting the background phase, in accordance with the following equation:

$$\cos(\phi_{cor}) = \text{real}[S_{cor}/|S_{cor}|]$$

In step Sd3, the computation unit 11 excludes regions of, for example, air in an amplitude image. Specifically, the phase of a voxel in a portion having a small signal such as air is random, so that processing such as threshold processing is performed for the amplitude image to create a mask corresponding to the air region. Then, this mask is used to perform mask processing for the BB image in order to exclude the air region from the amplitude image. Specifically, this mask processing brings an image value $S_{mask}$ of each pixel after masking into Mask×$S_{orig}$, wherein for each pixel of the amplitude image, Mask=1 when an amplitude value A is equal to or more than a threshold value Th, or Mask=0 otherwise.

In step Sd4, the computation unit 11 generates a cosine filter $H_B = H\{\cos(\phi_{cor}), n\}$ as a function for the normalized real part signal and an enhancement factor n.

$$H_B = 2 \times [M^n - 0.5]$$

Here, the cosine filter includes an asymmetric type and a symmetric type. M for the asymmetric type is determined as in the following equation if $\text{Im}[S_{cor}] < 0$ or $\phi_{cor} < 0$ is satisfied when Im is an operator extracting imaginary part. If any of these conditions is not satisfied, M is 1.

$$M = \{\cos(\phi_{cor}) + 1\}/2$$

M for the symmetric type is unconditionally determined as in the following equation:

$$M = \{\cos(\phi_{cor}) + 1\}/2$$

Furthermore, the enhancement factor n is a value equal to or more than 1. Enhancement is stronger when the enhancement factor n is greater. In addition, $H_B$ is 1 if n=0, which corresponds to amplitude. $H_B$ is $\cos(\phi_{cor})$ if n=1, which simply corresponds to a normalized real part. Moreover, the symmetric type is suitable when the enhancement factor n is not so great and when TE is sufficiently short and thus the effect of susceptibility is negligible. Otherwise, the asymmetric type is suitable.

Figure 28:
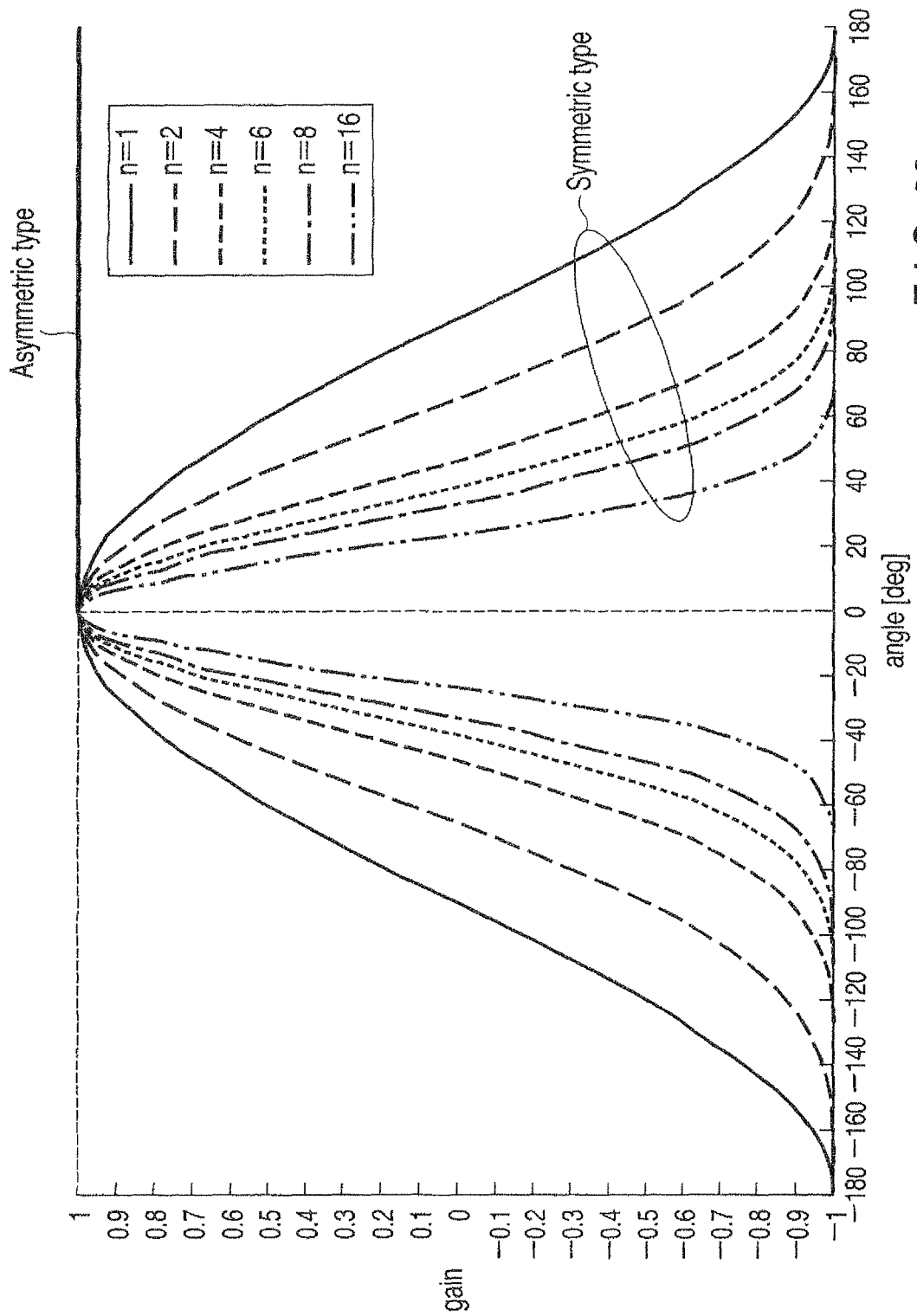
FIG. 28 is a graph showing one example of the characteristics of a cosine filter.

FIG. 28 is a graph showing the characteristics of the cosine filter.

In step Sd5, the computation unit 11 applies the cosine filter generated in step Sd4 to an amplitude image $A_{orig}$, and thereby obtains an image value $I_{cor}$ of the corrected BB image. That is, the image value I is found by the following equation:

$$I_{cor} = A_{orig} \times H_B$$

Figure 30:
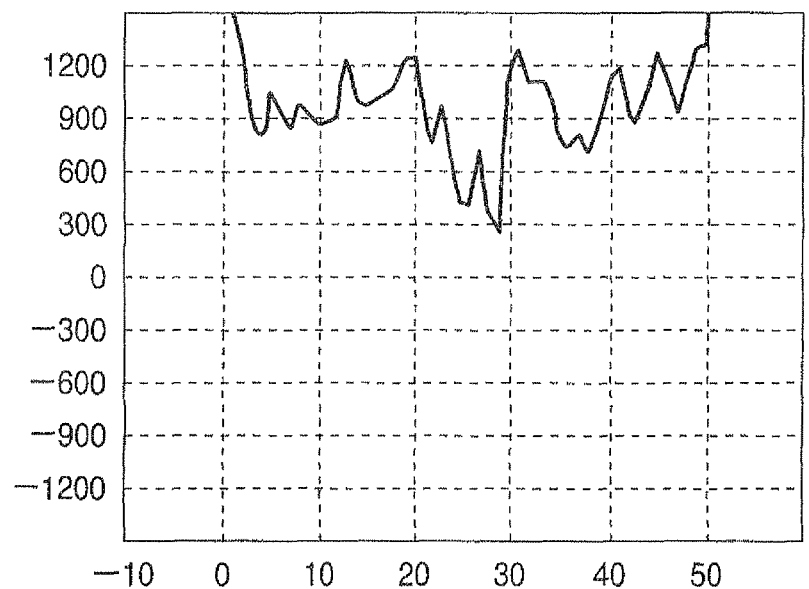
FIG. 30 is a graph showing the profile of an image value at the position of a white line indicated in the image on the left in FIG. 29.
Figure 31:
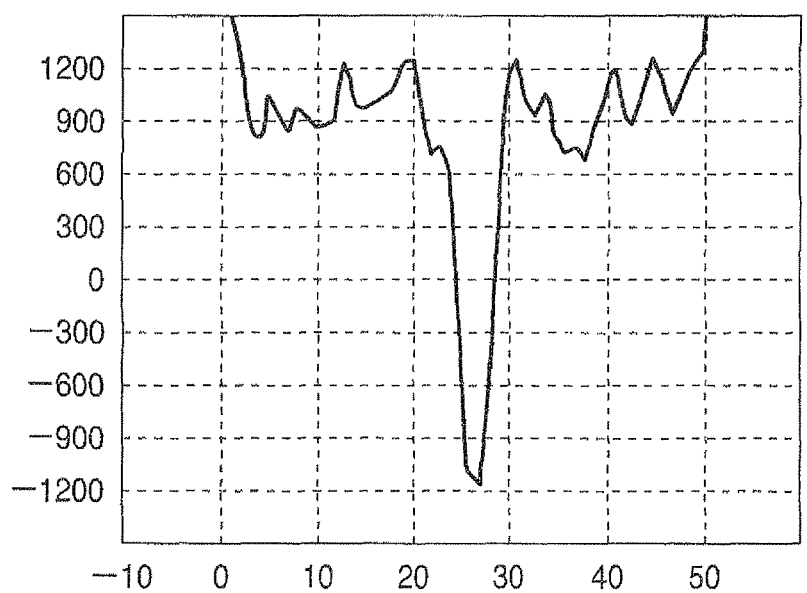
FIG. 31 is a graph showing the profile of an image value at the position of a white line indicated in the image on the right in FIG. 29.

FIG. 29 is a view showing a real part image obtained by a conventional FS-BB method and a real part image obtained by the third embodiment. The real part image obtained by the conventional FS-BB method is on the left in FIG. 29, and the real part image obtained by the third embodiment is on the right. FIG. 30 is a graph showing the profile of an image value at the position of a white line indicated in the image on the left in FIG. 29. FIG. 31 is a graph showing the profile of an image value at the position of a white line indicated in the image on the right in FIG. 29.

As is apparent from FIG. 29 to FIG. 31, according to the operation of the MRI apparatus 100 in the third embodiment, the BB image in which the return of the amplitude shown in FIG. 5 is eliminated. Thus, as in the first embodiment, the contrast of the blood vessel to the background portion can be further increased than in the case where the BB image in which the return of the amplitude shown in FIG. 5 is generated is used as-is.

Moreover, the BB image having such an increased contrast is used to calculate a scaling difference between the WB image and the BB image as in the first embodiment, such that a hybrid MRA image having a higher contrast than in the first embodiment can be generated.

Furthermore, according to the third embodiment, the image value is enhanced by a phase component through a calculation using the real part in the complex signal. Therefore, there is no need to obtain the phase φ contrary to the first embodiment, so that loads on the computation unit 11 can be less than in the first embodiment.

Still further, according to the third embodiment, the value of $M(\cos(\phi_{cor}))$ can be changed to selectively apply the asymmetric type cosine filter and the symmetric type cosine filter.

Further yet, according to the third embodiment, the value of the enhancement factor n can be greater than 0, such that enhancement processing using the real part can be performed, which leads to a further improvement in contrast. Moreover, the value of the enhancement factor n can be adjusted to adjust the intensity of the enhancement processing using the real part.

(Fourth Embodiment)

The phase of a blood vessel flow component of a second moment or higher order moment is not zero in the primary GMN, and the phase of a blood vessel flow component of a first moment or higher order moment is not zero either in the zeroeth GMN. Thus, in the fourth embodiment, information on these phases is used to further improve the contrast in the WB image. That is, in the fourth embodiment, the blood vessel visualizing capability is improved by the effective use of a flow component of an order higher than the order of rephasing by the GMN applied in the TOF method. In other words, the phase of a blood vessel flow component of a flow equal to or more than (n+1)-th moment is not zero in the case of the nth GMN, so that information on this phase is added to amplitude information to increase the signal amplitude of a blood flow portion.

Figure 32:
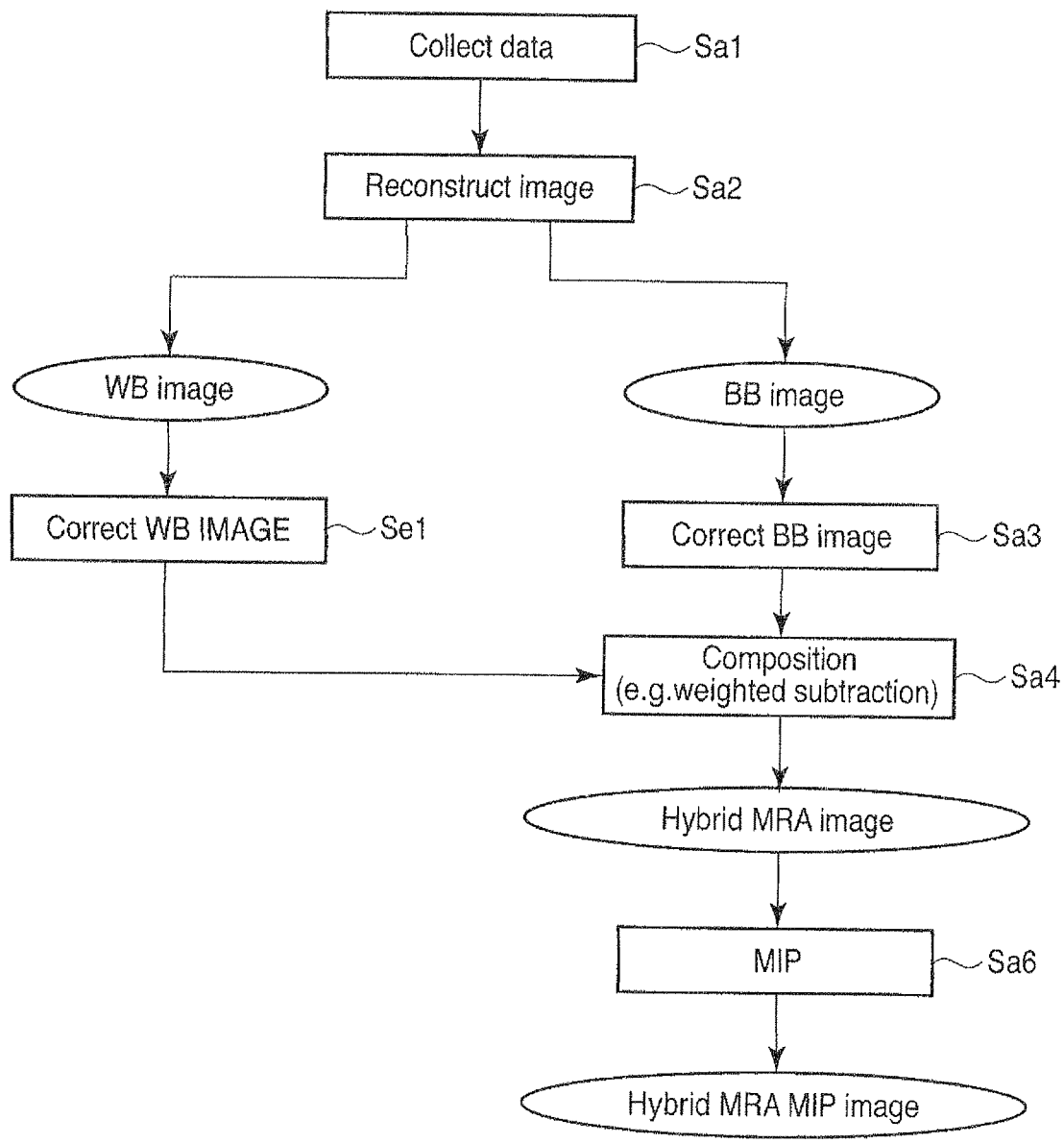
FIG. 32 is a flowchart showing a procedure for operating the MRI apparatus shown in FIG. 1 to obtain hybrid MRA in a second embodiment.

FIG. 32 is a flowchart showing a procedure for operating the MRI apparatus 100 to obtain hybrid MRA in the fourth embodiment. It should be noted that steps for the same processing as the steps in FIG. 2 are provided with the same signs and are not described later.

As is apparent from the comparison between FIG. 32 and FIG. 2, the operation of the MRI apparatus 100 in the fourth embodiment is different from that in the first embodiment in that step Se1 is carried out to correct the WB image before the creation of a mask in step Sa5.

Figure 33:
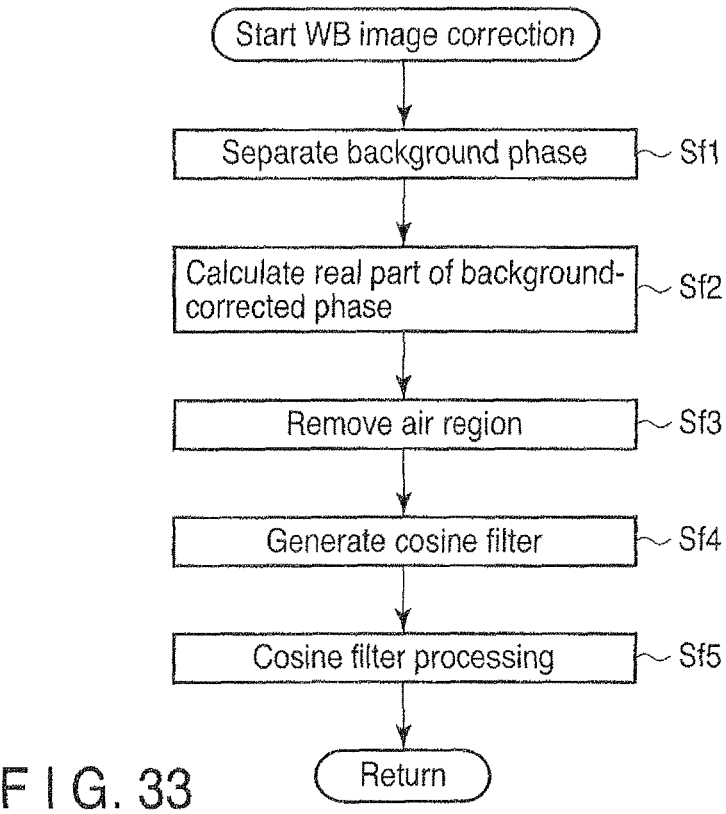
FIG. 33 is a flowchart showing a processing procedure in correcting a WB image by the computation unit in FIG. 1.

FIG. 33 is a flowchart showing a processing procedure of the computation unit 11 in correcting the WB image.

In step Sf1, the computation unit 11 excludes a low-frequency component having a non-uniform magnetic field by using, for example, a high pass filter (also referred to as a homodyne filter to obtain a complex signal $S_{cor}$ in which the background phase is corrected. That is, the complex signal $S_{cor}$ is found by the following equation:

$$S_{cor} = S_{orig} \times S_{low}*/|S_{low}|$$

wherein $S_{orig}$ is an original complex signal, $S_{low}$ is a complex signal obtained by filtering $S_{orig}$ with a low pass filter, and $S_{low}^*$ is a complex conjugate of the complex signal $S_{low}$.

In step Sf2, the computation unit 11 obtains a real part signal $\cos(\phi_{cor})$ that is normalized by correcting the background phase, in accordance with the following equation:

$$\cos(\phi_{cor}) = \text{real}[S_{cor}/|S_{cor}|]$$

In step Sf3, the computation unit 11 excludes regions of, for example, air in an amplitude image. Specifically, the phase of a voxel in a portion having a small signal such as air is random, so that processing such as threshold processing is performed on the amplitude image to create a mask corresponding to the air region. Then, this mask is used to perform mask processing for the WB image in order to exclude the air region from the amplitude image. Specifically, this mask processing brings an image value $S_{mask}$ of each pixel after masking into $Mask \times S_{orig}$, wherein for each pixel of the amplitude image, Mask=1 when an amplitude value A is equal to or more than a threshold value Th, or Mask=0 otherwise.

In step Sf4, the computation unit 11 generates a cosine filter $H_W = H\{\cos(\phi_{cor}), n\}$ as a function for the normalized real part signal and n.

$$H_W = 1 + (k-1) \times (1 - M^n)$$

Note that M is a value found when $\{1 + \cos(\phi_{cor})\}/2$. k is the maximum multiplication of the cosine filter. n is an enhancement factor and is a value equal to or more than 1. Enhancement is stronger when n is greater.

That is, the cosine filter is generated as a filter in which the maximum value of a gain is 1 and the minimum value is k.

Figure 34:
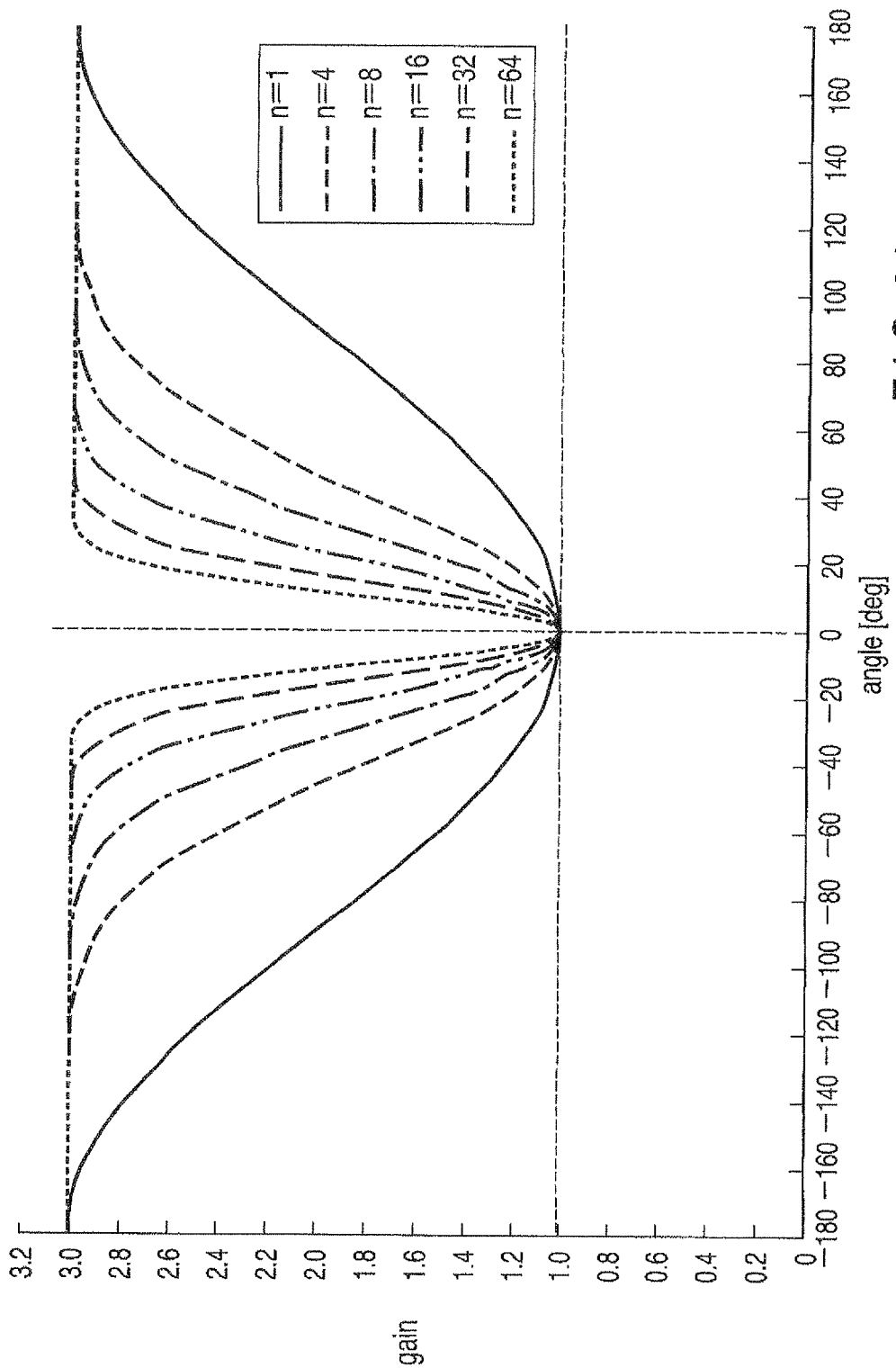
FIG. 34 is a graph showing one example of the characteristics of the cosine filters.

FIG. 34 is a graph showing one example of the characteristics of the cosine filters.

The characteristics shown in FIG. 34 are associated with six kinds of cosine filters, wherein k is fixed at 3 and n is 1, 4, 8, 16, 32, 64.

In step Sf5, the computation unit 11 applies the cosine filter generated in step Sf4 to an amplitude image $A_{orig}$, and thereby obtains an image value $I_{cor}$ of the corrected WB image. That is, the image value I is found by the following equation:

$$I_{cor} = A_{orig} \times H_W$$

That is, the amplitude is A, the phase is $\phi$, and the complex signal S of a voxel is represented by $S = A * \exp[j\phi]$. Then, filter processing is performed so that A may be greater as $\phi$ becomes farther from 0.

Thus, according to the fourth embodiment, enhancement is made on the basis of the phase contained in the blood vessel flow component of a flow equal to or more than (n+1)-th moment in nth GMN, such that the contrast between the blood vessel portion and the background portion in the WB image is improved.

Moreover, the WB image having such an increased contrast is used to calculate a scaling difference between the WB image and the BB image as in the first embodiment, such that a hybrid MRA image having a higher contrast than in the first embodiment can be generated.

In addition, in this fourth embodiment, TE can be reduced, and the phase contained in the blood vessel flow component is higher, so that the maximum effect can be obtained when the zeroeth GMN is applied. However, when the nth GMN (n is 1 or more) to which even rephases higher order moments is applied, the image value based on a phase component of n+1 order or higher is enhanced, and some effects can be expected. For example, even in the primary GMN, components of a second order or higher order such as a turbulent flow are enhanced.

The following various modifications of this embodiment can be made.

(1) The background phase may be obtained not from its own data but from other data.

For example, it is possible to use a phase map that is created by use of a shimming sequence having an extremely low sensitivity to flow. These days, in order to constrain fat or stabilize an image obtained by echo planar imaging (EPI), it is often the case that each patient is imaged in a routine manner to acquire the above-mentioned phase map. Thus, new imaging for creating a phase contrast map is not necessary in terms of time, and there is no problem in terms of time.

A combination of in-phase TEs for water and fat is used in two echoes (TE=TE1, TE2) in a GRE method. If the chemical shift of water/fat is 3.5 ppm, TE1=4.5 ms and TE2=9.0 ms when the strength of a static magnetic field is 1.5 T.

(2) The background phase obtained by shimming or by the image with GMN has no contribution of flow and predominantly includes components attributed to the non-uniformity of a magnetic field. If these components are used to correct the background phase, the result can be regarded as substantially reflecting the original phase. However, especially in the phase that is obtained by the difference produced by the comparison with the low pass filter, the phase of a blood vessel is underestimated. To be closer to the original phase, phase enhancement processing based on the following linear windowing may be performed together. However, such processing is not necessary if the linear relation of the phases should be preserved.

Figure 35:
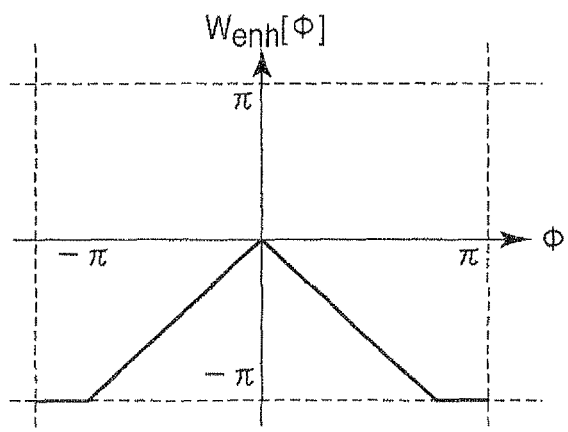
FIG. 35 is a graph showing a modification of the window function.

That is, in order to be closer to the original phase or to preserve a linear magnitude relation of the blood vessel phases, a window function as shown in FIG. 35, for example, is used for scaling so that each of the positive and negative maximum phases may be ±180°.

In addition, a phase obtained by a low pass filter difference is dependent on the size of a blood vessel and is not precise. If blood vessels have the same size, the magnitude relation of phases, that is, the magnitude relation of blood flow velocities is substantially maintained.

A nonlinear window function is applied so that the maximum phase may be closer to 180 degrees. In this case, the magnitude relation of phases is neglected, and the blood vessel contrast is enhanced anyway.

(3) In both the first and second embodiments, the phase enhancement processing can be omitted.

(4) In the first to third embodiments, in order to improve the contrast between the blood vessel and the static portion in the hybrid MRA image, the contrast between the blood vessel and the static portion in the BB image used to generate the hybrid MRA image is improved. However, even when a BB image is separately obtained independently of the hybrid MRA image, the present technique can be used to improve the contrast between the blood vessel and the static portion in this BB image.

(5) The cosine filter in the third embodiment is also applicable to the FS-BB method (dephase) or to the BB method based on rephasing.

(6) The characteristics of the cosine filters in the fourth embodiment are not limited to the characteristics shown in FIG. 34. The cosine filter has only to be configured to enhance a component whose phase is not zero rather than a component whose phase is zero. Therefore, other phase enhancement filters having no cosine characteristics may be used instead of the cosine filter.

(7) In the fourth embodiment, in order to improve the contrast between the blood vessel and the static portion in the hybrid MRA image, the contrast between the blood vessel and the static portion in the WB image used to generate the hybrid MRA image is improved. However, even when a WB image is separately obtained independently of the hybrid MRA image, the present technique can be used to improve the contrast between the blood vessel and the static portion in this WB image.

(8) If a hybrid MRA image is generated as the difference between the BB image subjected to the enhancement processing in the third embodiment and the WB image subjected to the enhancement processing in the fourth embodiment, an MRA image having a higher contrast than in any of the first to fourth embodiments can be obtained.

(9) The characteristic processing in each of the embodiments described above can be performed for raw data.

(10) All the techniques in the embodiments described above are also applicable to the generation of an image that shows a normal portion of a background and an abnormal portion different in susceptibility from the normal portion with a contrast therebetween. Clinically, the abnormal portion includes a part that has coagulated blood, a part having multiple sclerosis, or a part having a basal nucleus changed with age.

(11) In the embodiments described above, the processing for the WB image and the BB image is performed as part of the imaging operation in the MRI apparatus 100. Thus, which of the two images is the WB image or the BB image can be easily known by the host computer 16. However, when the processing for at least one of the WB image and the BB image is performed as post-processing, it is necessary to determine whether an image indicated by image data stored in the storage unit 12 is a WB image or a BB image. This determination can be carried out on the basis of the kind of sequence and parameters (e.g., TR, TE and a b value) applied during imaging. Alternatively, information indicating whether an image is a WB image or a BB image may be added to collateral information during imaging, and on the basis of this information, whether the image is a WB image or a BB image may be determined during post-processing.

(12) At least part of the processing for a WB image, the processing for a BB image or the processing for generating a hybrid MRA image may be performed by a medical image processing apparatus that differs from an MRI apparatus. That is, the various aspects of the invention of the present application can also be achieved by a medical image processing apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging (MRI) apparatus comprising:
   static and gradient magnetic field generators, at least one radio frequency (RF) coil disposed within said magnetic field generators, RF transmit and receive circuits coupled to said RF coil, and MM sequence and computation circuits, including digital memory and at least one data processor, configured to control said gradient magnetic field generators and said RF transmit and receive circuits to
   detect a first magnetization vector for each of a large number of pixel positions in an imaging region including at least part of a subject, the first magnetization vector being excited (a) to have a higher amplitude in a flow portion in which a fluid flows than in a static portion in which tissues are static or (b) to have a higher amplitude in an abnormal portion different in susceptibility from a normal portion and (c) to have a phase difference between (i) the flow and static portions or (ii) the abnormal and normal portions;
   generate first image data having first image data contrast, the first image data including, as a first pixel value of each pixel position, a value proportional to an absolute value of an amplitude of the first magnetization vector detected for each of the large number of pixel positions;
   detect a second magnetization vector for each of the large number of pixel positions, the second magnetization vector being excited (a) to have a lower amplitude in the flow portion than in the static portion or to have a lower amplitude in the abnormal portion than in the static portion and (b) to have a phase difference between the flow and static portions or the abnormal and normal portions;
   generate second image data having second image data contrast, the second image data including, as a second pixel value of each pixel position, a value proportional to an absolute value of an amplitude of the second magnetization vector detected for each of the large number of pixel positions;
   correct at least one of the first and second image data so that a difference of the pixel values increases between (a) the flow and static portions or (b) the abnormal and normal portions wherein if the first image data is corrected, it is corrected on the basis of a real part or phase of the first magnetization vector detected for each of the large number of pixel positions, and if the second image data is corrected, it is corrected on the basis of a real part or phase of the second magnetization vector detected for each of the large number of pixel positions; and
   generate third image data in which contrast between (a) the flow and static portions or (b) the abnormal and normal portions is higher than in the first and second image data,
   the third image data being generated on the basis of the first image data as corrected and the second image data when only the first data is corrected,
   the third image data being generated on the basis of the first image data and the second image data as corrected when only the second data is corrected,
   the third image data being generated on the basis of the corrected first image data and the second image data when both the first and second image data have been corrected.

2. The magnetic resonance imaging apparatus according to claim 1, wherein at least one of the first and second detections uses an MRI data acquisition sequence having a shortened echo time for zeroeth gradient moment nulling (GMN).

3. The magnetic resonance imaging apparatus according to claim 1, wherein:
   for correction of the first image data, a first amplitude image of the subject is generated on the basis of an amplitude component in the first magnetization vector, a real part of a background phase of the first magnetization vector is obtained from a complex signal which is obtained from the first magnetization vector, a first cosine filter is generated on the basis of a real part of a background phase of the first magnetization vector, and the first cosine filter is applied to the first amplitude image to obtain an image in which the real part of the background phase is corrected; and for correction of the second image data, a second amplitude image of the subject is generated on the basis of an amplitude component in the second magnetization vector, a real part of a background phase of the second magnetization vector is obtained from a complex signal which is obtained from the second magnetization vector, a second cosine filter is generated on the basis of a real part of a background phase of the second magnetization vector, and the second cosine filter is applied to the second amplitude image to obtain an image in which the real part of the background phase is corrected.

4. The magnetic resonance imaging apparatus according to claim 3, wherein the first or second cosine filter is generated so that enhancement processing using the real part is performed by applying the first or second cosine filter to the amplitude image.

5. The magnetic resonance imaging apparatus according to claim 4, wherein the cosine filter is applied to the first and/or second amplitude image, if corrected, after correction so that a phase shifted by a spatial frequency is changed to an original phase.

6. The magnetic resonance imaging apparatus according to claim 3, wherein the first and second cosine filters are generated so that enhancement processing using a real part of a complex value is performed by applying each of the first and second cosine filters to a respectively corresponding amplitude image.

7. The magnetic resonance imaging apparatus according to claim 6, wherein the first or second cosine filter is applied to a respective amplitude image after correction so that a phase shifted by a spatial frequency is brought to an original phase.

8. The magnetic resonance imaging apparatus according to claim 7, wherein a single echo type time of flight (TOF) method is used for detecting the magnetization vector.

9. The magnetic resonance imaging apparatus according to claim 1, wherein:

a background phase attributed to the static portion or the normal portion is obtained for each of the large number of pixel positions, a corrected phase of each pixel position is calculated as a phase in which the background phase is excluded from the phase of the magnetization vector detected for each of the large number of pixel positions, and the pixel value of the pixel position is corrected where the calculated corrected phase is not zero.

* * * * *